US012138023B2

(12) United States Patent
Nishida et al.

(10) Patent No.: US 12,138,023 B2
(45) Date of Patent: Nov. 12, 2024

(54) BLOOD PRESSURE MEASUREMENT DEVICE

(71) Applicants: OMRON CORPORATION, Kyoto (JP); OMRON HEALTHCARE CO., LTD., Muko (JP)

(72) Inventors: Tomoyuki Nishida, Kyoto (JP); Hirokazu Tanaka, Otsu (JP); Shinji Mizuno, Yasu (JP); Noboru Kohara, Okayama (JP); Kotaro Kitajo, Saitama (JP); Keitaro Nagano, Kyoto (JP); Yoshihiko Sano, Kyoto (JP); Takashi Ono, Kyoto (JP)

(73) Assignees: OMRON CORPORATION, Kyoto (JP); OMRON HEALTHCARE CO., LTD., Kyoto (JP)

( * ) Notice: Subject to any disclaimer, the term of this patent is extended or adjusted under 35 U.S.C. 154(b) by 427 days.

(21) Appl. No.: 16/930,166

(22) Filed: Jul. 15, 2020

(65) Prior Publication Data
US 2020/0345248 A1    Nov. 5, 2020

Related U.S. Application Data

(63) Continuation of application No. PCT/JP2019/000345, filed on Jan. 9, 2019.

(30) Foreign Application Priority Data

Jan. 15, 2018  (JP) ................. 2018-004484

(51) Int. Cl.
*A61B 5/021* (2006.01)
*A61B 5/00* (2006.01)
(Continued)

(52) U.S. Cl.
CPC ........ *A61B 5/02141* (2013.01); *A61B 5/0225* (2013.01); *A61B 5/0235* (2013.01);
(Continued)

(58) Field of Classification Search
CPC . A61B 5/02141; A61B 5/0225; A61B 5/0235; A61B 5/681; A61B 5/6832;
(Continued)

(56) References Cited

U.S. PATENT DOCUMENTS 5,687,732 A * 11/1997 Inagaki .............. G04B 37/0016
                                                600/490
7,780,698 B2 * 8/2010 McEwen .............. A61B 17/135
                                                606/203

(Continued)

FOREIGN PATENT DOCUMENTS

CN         1128648 A    8/1996
JP      2006-158543 A    6/2006
(Continued)

OTHER PUBLICATIONS

Gutierrez, Measurements of Elastic Moduli of Silicone Gel Substrates with a Microfluidic Device, 2011, Plos One, vol. 6 | Issue 9, pp. 1-8. (Year: 2011).*

(Continued)

*Primary Examiner* — Benjamin S Melhus
*Assistant Examiner* — Severo Antonio P Lopez
(74) *Attorney, Agent, or Firm* — Oliff PLC

(57) ABSTRACT

A blood pressure measurement device includes: a case including an outer case, a base housed in the outer case, and a back cover that covers an opening of the outer case; a movable portion arranged in a gap between the outer case, the base and the back cover, and including a bag-shaped cuff that inflates when a fluid is supplied to an internal space; and a seal member that is formed of a gel body having a lower elastic modulus than that of the cuff, and that is provided in the gap to seal the gap.

2 Claims, 20 Drawing Sheets

(51) Int. Cl.
*A61B 5/0225* (2006.01)
*A61B 5/0235* (2006.01)
(52) U.S. Cl.
CPC ............ *A61B 5/681* (2013.01); *A61B 5/6832* (2013.01); *A61B 5/742* (2013.01); *A61B 2560/0214* (2013.01); *A61B 2562/0247* (2013.01)
(58) Field of Classification Search
CPC ......... A61B 5/742; A61B 5/022; A61B 5/021; A61B 2560/0214; A61B 2562/0247
USPC ....................................................... 600/492
See application file for complete search history.

(56) References Cited

U.S. PATENT DOCUMENTS

| | | | |
|---|---|---|---|
| 2006/0184054 A1* | 8/2006 | Sano | A61B 5/021 600/490 |
| 2015/0094552 A1* | 4/2015 | Golda | A61B 5/02125 600/336 |
| 2015/0351851 A1* | 12/2015 | Deselle | A61B 5/02233 600/490 |
| 2016/0287102 A1* | 10/2016 | Saponas | A61B 5/02108 |
| 2017/0311814 A1* | 11/2017 | Lu | A61B 5/02141 |

FOREIGN PATENT DOCUMENTS

| | | |
|---|---|---|
| JP | 2013-220187 A | 10/2013 |
| JP | 2014-033829 A | 2/2014 |
| JP | 2016-047086 A | 4/2016 |

OTHER PUBLICATIONS

Young Modulus, Omnexus by SpecialChem, Dec. 19, 2015. (Year: 2015).*

Apr. 2, 2019 International Search Report issued in International Patent Application No. PCT/JP2019/000345.

Jan. 3, 2023 Office Action issued in Chinese Patent Application No. 201980007652.9.

* cited by examiner

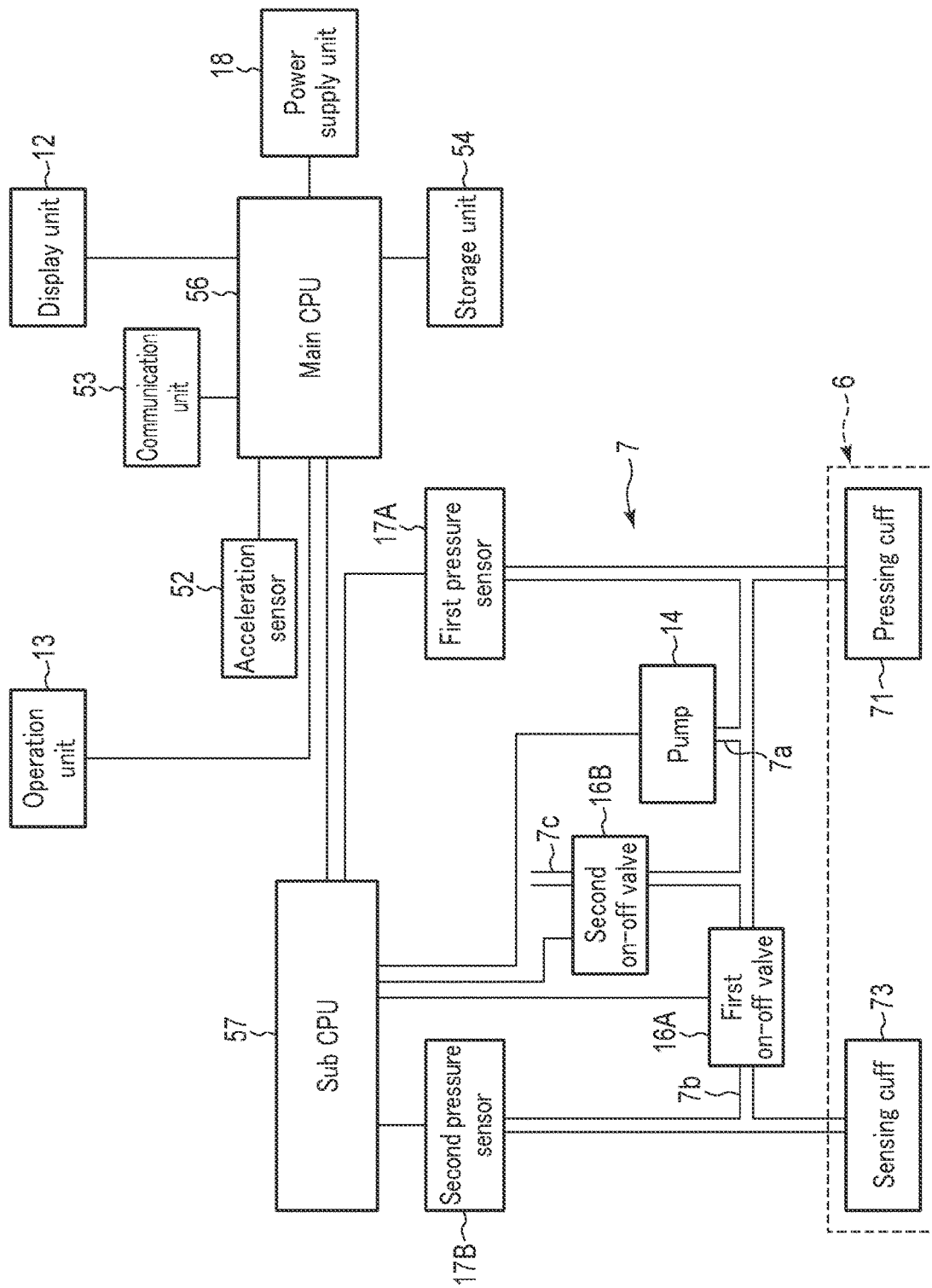
F I G. 4

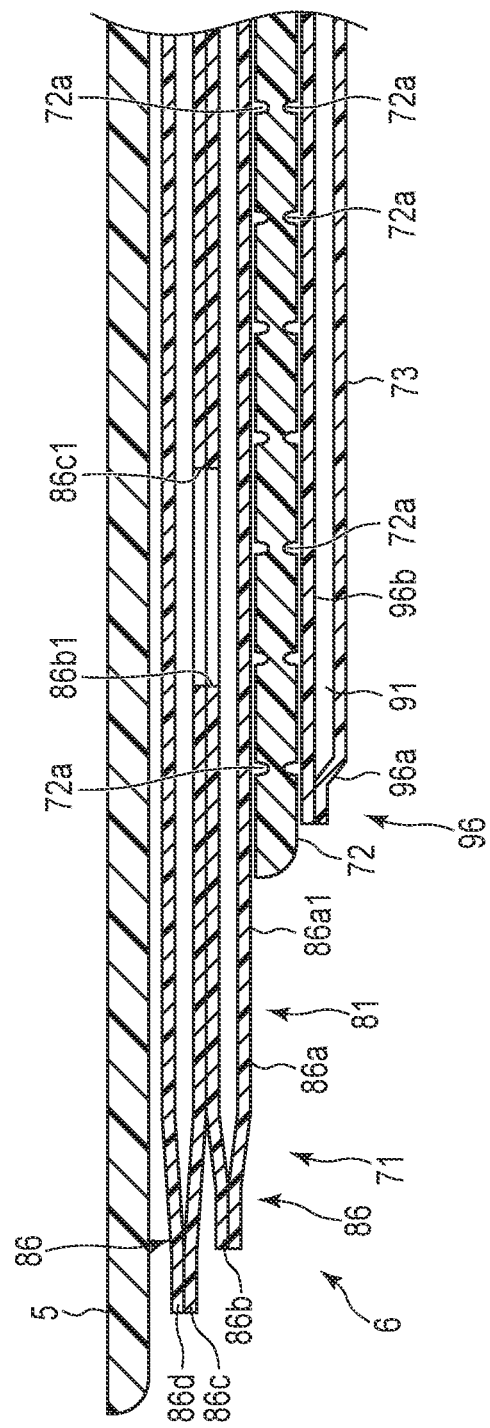
F I G. 12

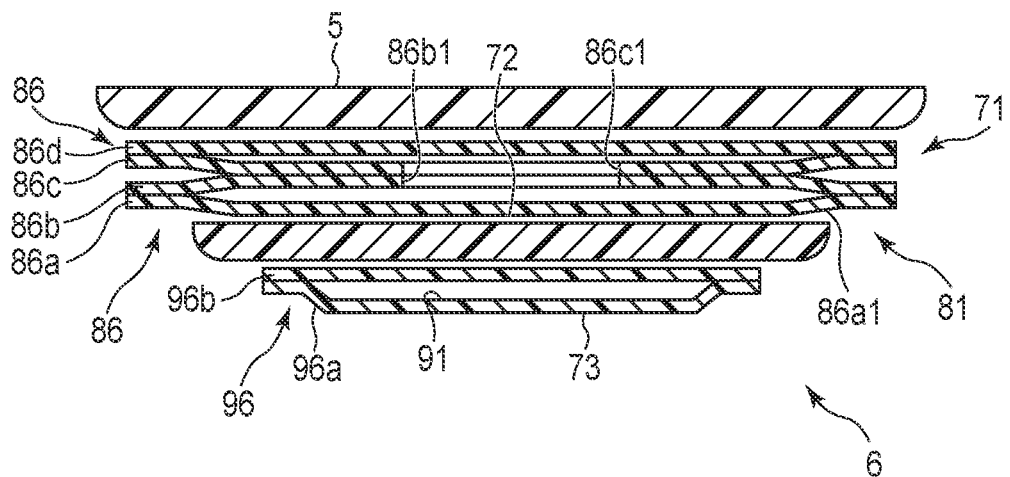
F I G. 13

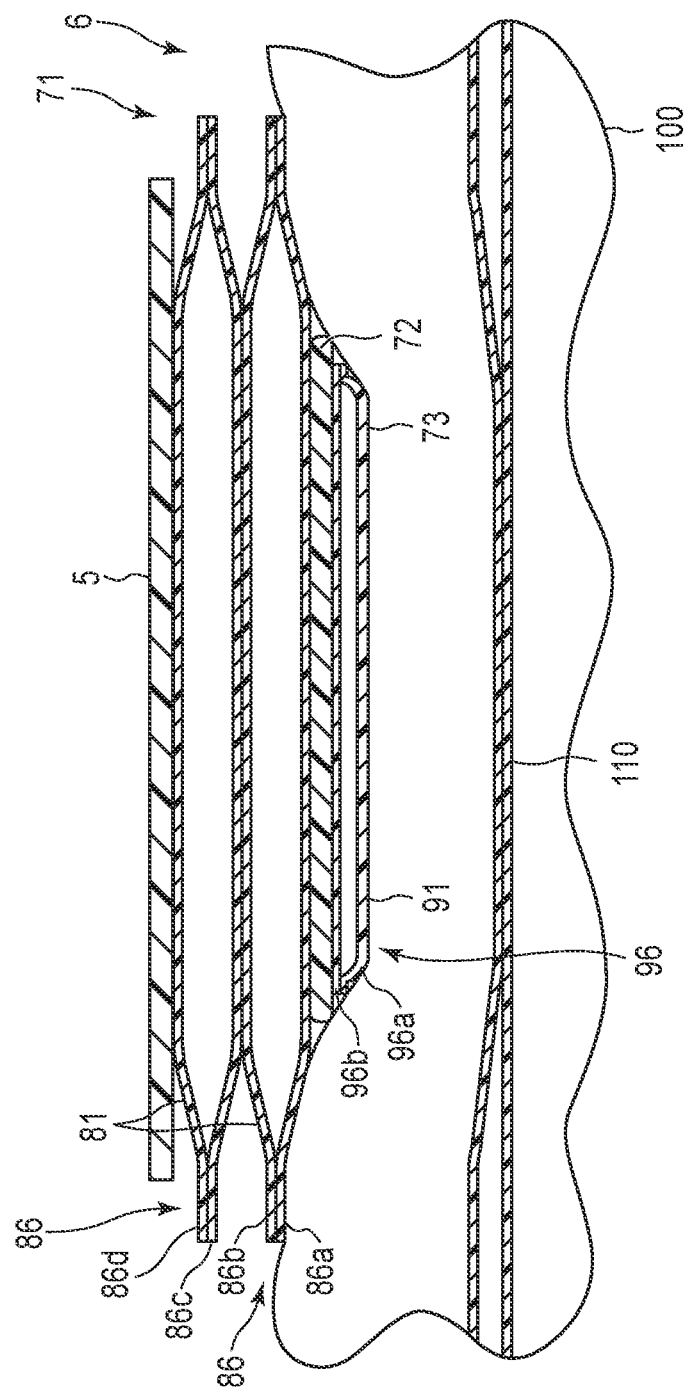
F I G. 15

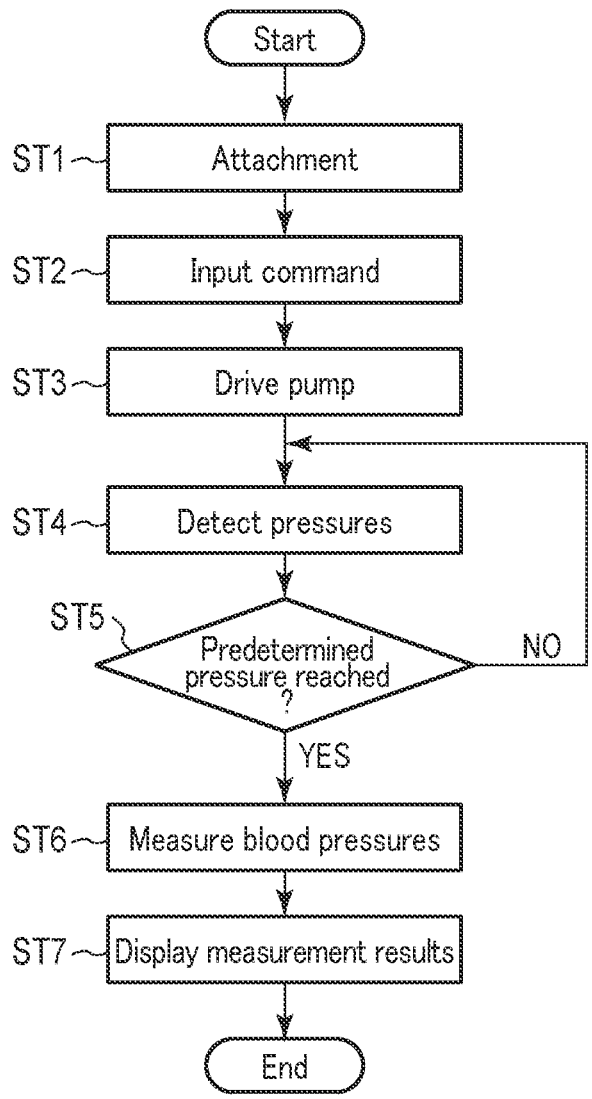
F I G. 16

BLOOD PRESSURE MEASUREMENT DEVICE

CROSS-REFERENCE TO RELATED APPLICATIONS

This is a Continuation Application of PCT application No. PCT/JP2019/000345, filed Jan. 9, 2019, which was published under PCT Article 21(2) in Japanese.

This application is based upon and claims the benefit of priority from Japanese Patent Application No. 2018-004484, filed Jan. 15, 2018, the entire contents of which are incorporated herein by reference.

BACKGROUND OF THE INVENTION

1. Field of the Invention

The present invention relates to a blood pressure measurement device that measures blood pressure.

2. Description of the Related Art

In recent years, blood pressure measurement devices used for measuring blood pressure are used not only in medical facilities but also at home as a means for confirming a health condition. A blood pressure measurement device measures blood pressure by detecting the vibration of the arterial wall, for example, by wrapping a cuff around the upper arm or wrist of a living body, inflating and contracting the cuff, and detecting the pressure of the cuff with a pressure sensor.

As a technique for fluidly connecting the cuff to the pump contained in the case of the blood pressure measurement device, a nozzle formed on the back surface of the case is used. The nozzle is fluidly connected to the pump within the case. The cuff is connected to the nozzle, and is thereby fluidly connected to the pump (see, for example, Jpn. Pat. Appln. KOKAI Publication No. 2013-220187).

It is required that the blood pressure measurement device be reduced in size. However, if the pump and the cuff are fluidly connected to each other by using the nozzle formed on the back surface of the case, the device body and the cuff are aligned in the thickness direction, and the reduction in size is restricted.

It is therefore conceivable to provide a blood measurement device whose size is reduced by adopting a configuration in which part of the cuff is housed in the case and in a gap formed in the case such that the cuff is fluidly connected to the pump.

BRIEF SUMMARY OF THE INVENTION

In a blood pressure measurement device in which a portion movable with respect to the case is arranged in the gap, water has to be prevented from entering the case through the gap, as in a blood pressure measurement device having a configuration in which part of the cuff is arranged in the gap formed in the case.

According to one aspect, there is provided a blood pressure measurement device including: a case including an outer case, a base housed in the outer case, and a back cover that covers an opening of the outer case; a movable portion arranged in a gap between the outer case, the base and the back cover, and including a bag-shaped cuff that inflates when a fluid is supplied to an internal space; and a seal member that is formed of a gel body having a lower elastic modulus than that of the cuff, and that is provided in the gap to seal the gap.

It should be noted here that the fluid includes liquid and air. When blood pressure is measured, the cuff is wrapped around the upper arm or wrist of a living body, and is inflated with a fluid supplied to the cuff. For example, the cuff is intended to include a pressing cuff and a sensing cuff of a blood pressure measurement device that measures blood pressure on the wrist, and a cuff of a blood pressure measurement device that measures blood pressure on the upper arm. Further, the cuff may be a bag-shaped structure such as an air bag constituting a pressing cuff. The movable portion is a portion that is displaced with respect to the case and includes a cuff. The cuff is displaced when the user wears the blood pressure measurement device. In the case where the blood pressure measurement device has a curler and the curler is arranged in a gap, the curler is regarded as a movable portion. It should be noted here that a gel body is a gel having such an elastic modulus as deforms itself when an external force is applied and can maintain the shape when no external force is applied.

According to this aspect, when the cuff wrapped around a living body is inflated, the seal member deforms in conformity with the cuff, so that the gap is kept sealed. Further, even if the cuff moves in the gap when the cuff is wrapped around the living body, the seal member deforms in conformity with this movement, so that the gap is kept sealed. In the case where the movable portion includes a curler, the curler may move within the gap when the curler is wrapped around the living body. Even so, the seal member deforms in conformity with the movement of the curler, and the gap is kept sealed.

In the blood pressure measurement device according to the above aspect, there is provided a blood pressure measurement device wherein the seal member includes a plurality of sheet members.

According to this aspect, the seal member can be easily provided in the gap by configuring the seal member with a plurality of sheet members in the gap.

In the blood pressure measurement device according to the above aspect, there is provided a blood pressure measurement device wherein a fixing member that fixes the seal member inside the gap.

A fixing member can be, for example, a double-sided adhesive tape or an adhesive agent.

According to this aspect, the seal member can be prevented from falling out of the gap.

Accordingly, it is possible to provide a blood pressure measurement device that can seal a gap in which a movable portion is arranged.

BRIEF DESCRIPTION OF THE SEVERAL VIEWS OF THE DRAWINGS

FIG. 4 is a block diagram showing a configuration of the blood pressure measurement device.

FIG. 12 is a cross-sectional view showing a configuration of a curler and the cuff structure both employed in the blood pressure measurement device.

FIG. 13 is a cross-sectional view showing a configuration of the curler and cuff structure body.

FIG. 15 is a cross-sectional view schematically showing how the pressing cuff of the cuff structure is when it is inflated.

FIG. 16 is a flowchart illustrating an example of how the blood pressure measurement device is used.

DETAILED DESCRIPTION OF THE INVENTION

Hereinafter, an example of the blood pressure measurement device 1 according to one embodiment of the present invention will be described with reference to FIGS. 1 to 19.

Figure 1:
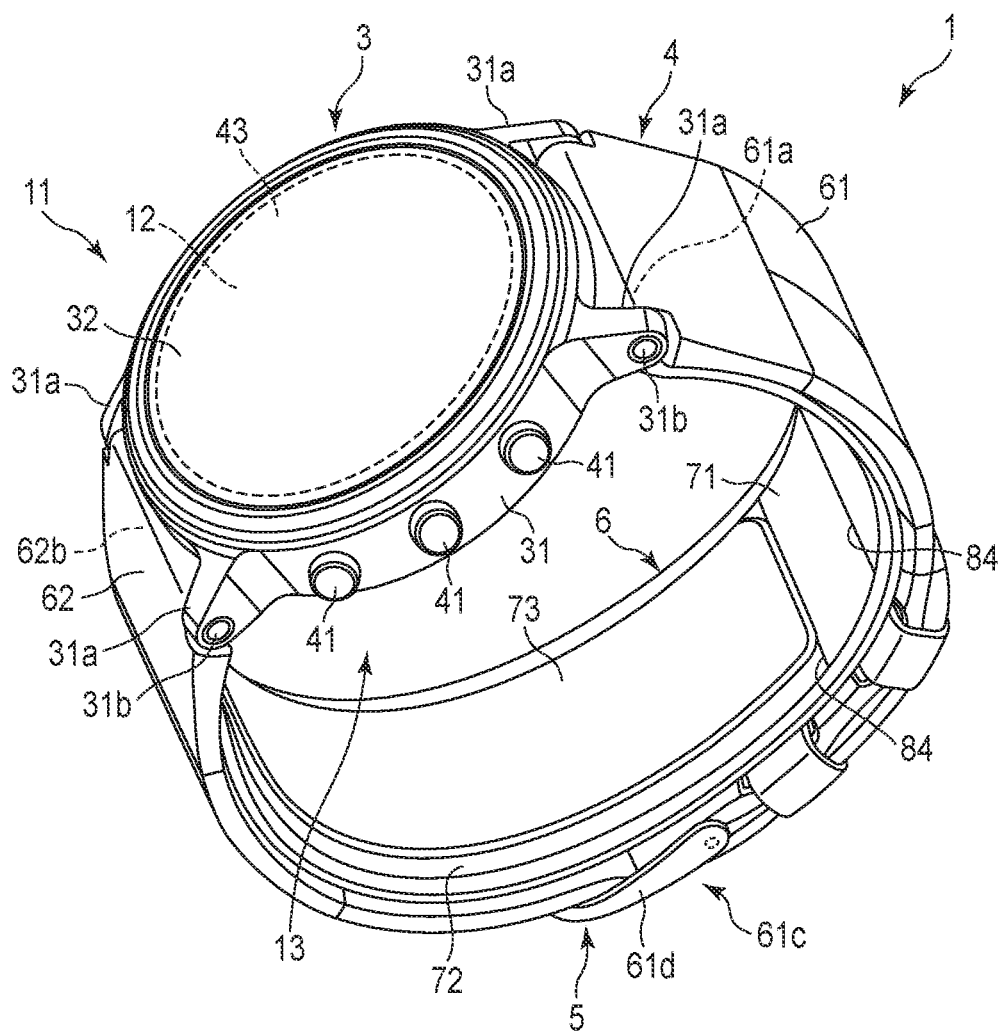
FIG. 1 is a perspective view showing a configuration of a blood pressure measurement device according to an embodiment of the present invention.
Figure 2:
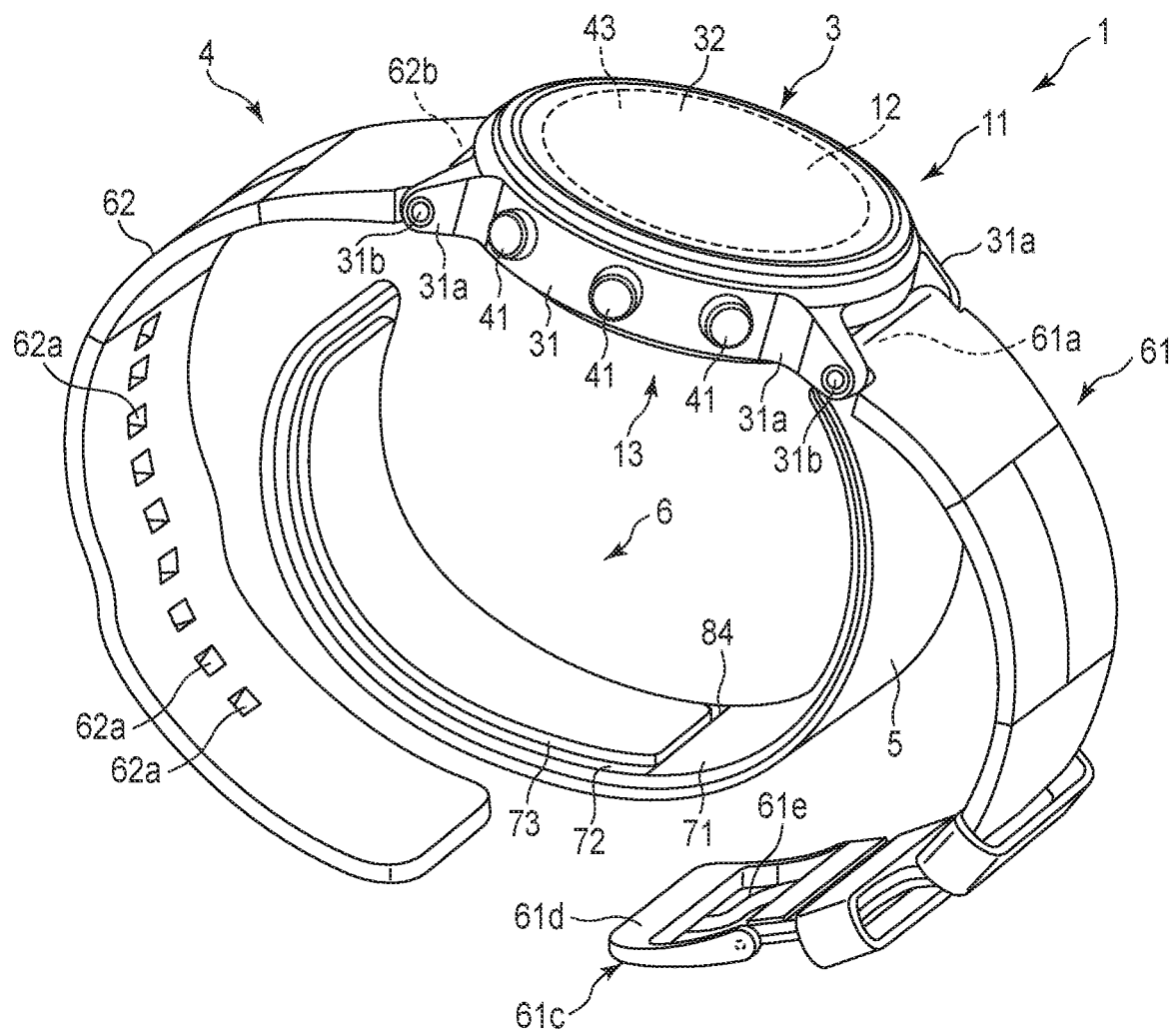
FIG. 2 is a perspective view showing a configuration of the blood pressure measurement device.
Figure 3:
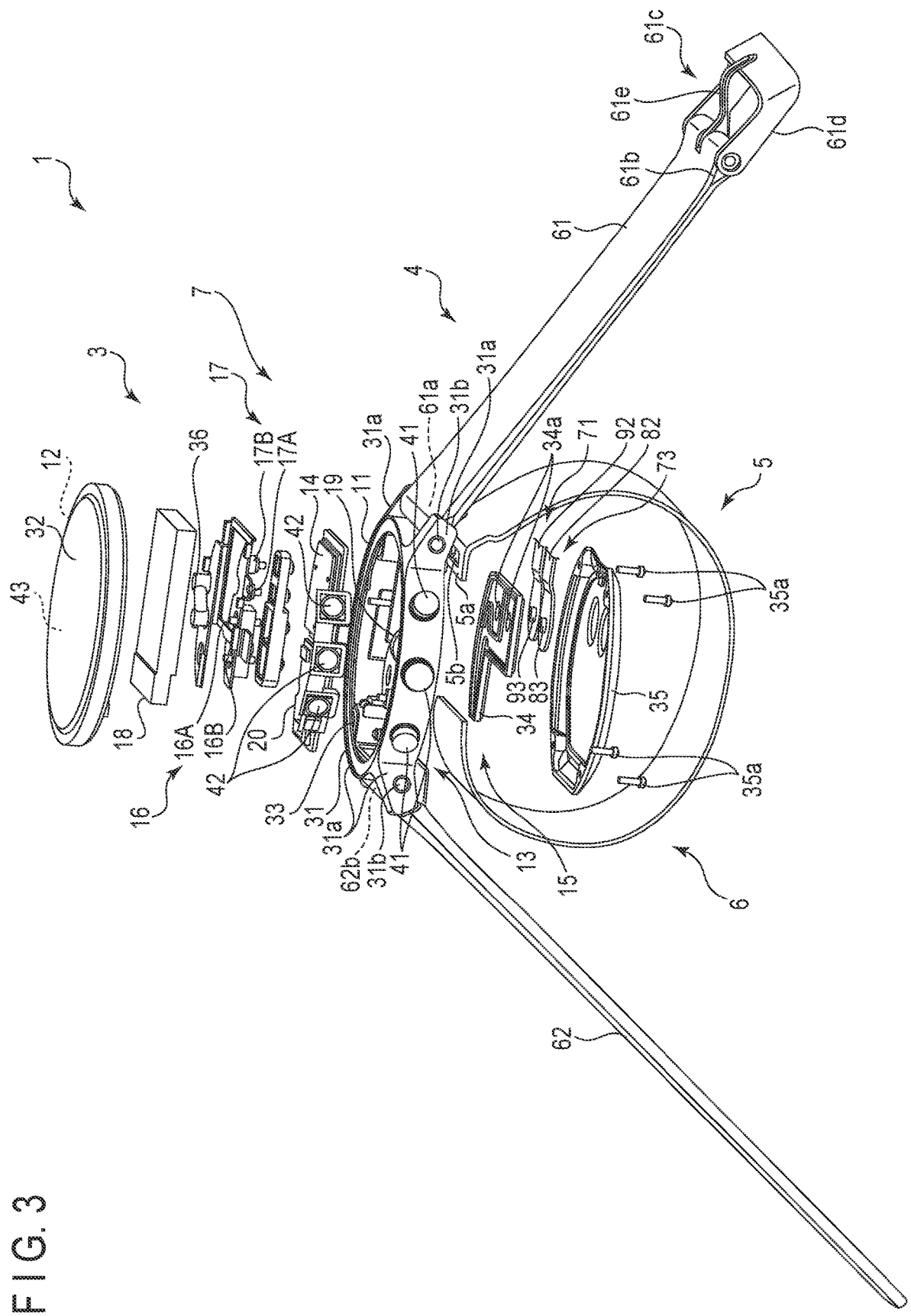
FIG. 3 is an exploded view showing a configuration of the blood pressure measurement device.
Figure 5:
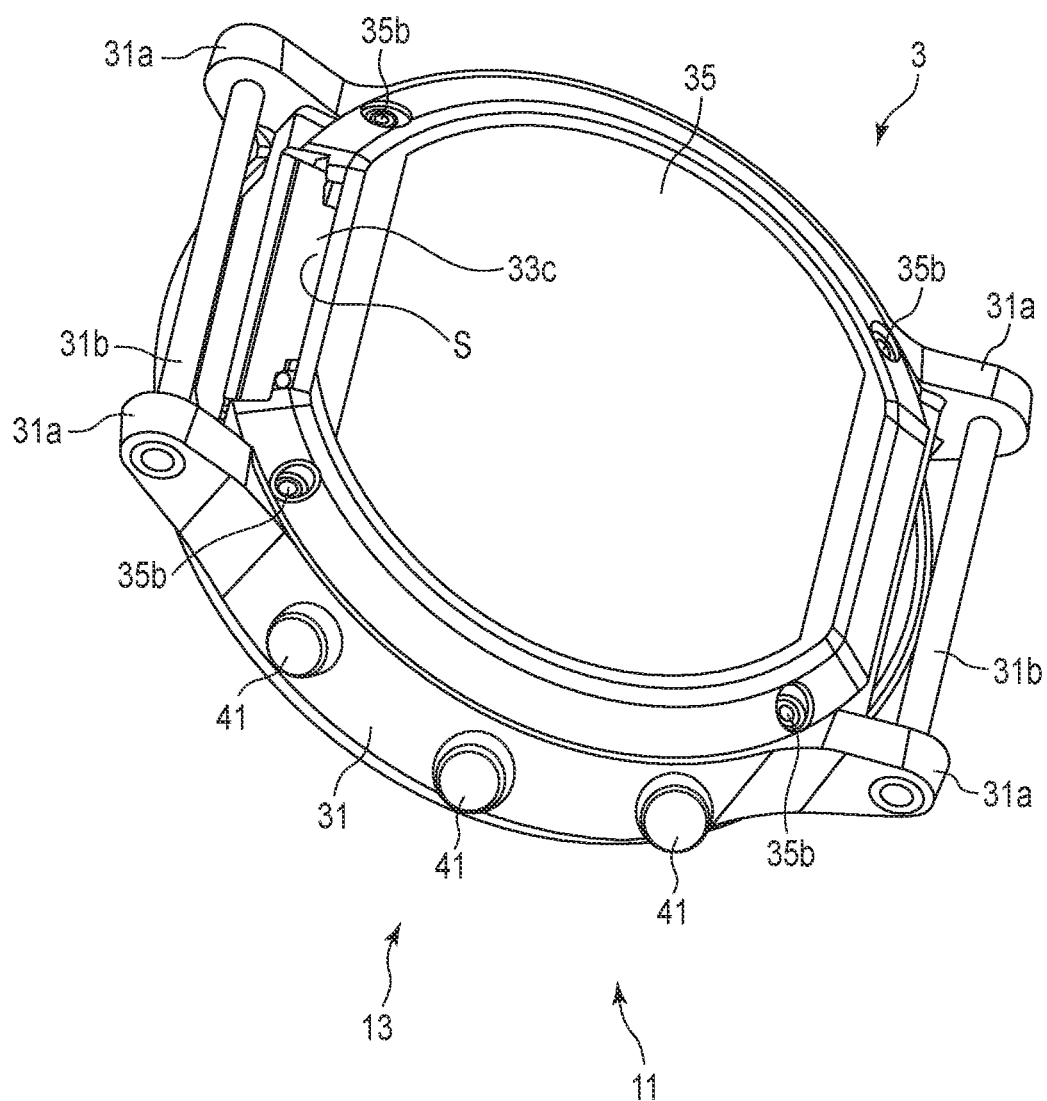
FIG. 5 is a perspective view showing a configuration of a device body of the blood pressure measurement device.

FIG. 1 is a perspective view showing how the blood pressure measurement device 1 according to one embodiment of the present invention looks like in a state where a strap 4 is closed. FIG. 2 is a perspective view showing how the blood pressure measurement device 1 looks like in a state where the strap 4 is open. FIG. 3 is an exploded view showing the configuration of the blood pressure measurement device 1. FIG. 4 is a block diagram showing the configuration of the blood pressure measurement device 1. FIG. 5 is a perspective view showing how the device body 3 of the blood pressure measurement device 1 looks like when viewed from the back cover 35 side.

Figure 6:
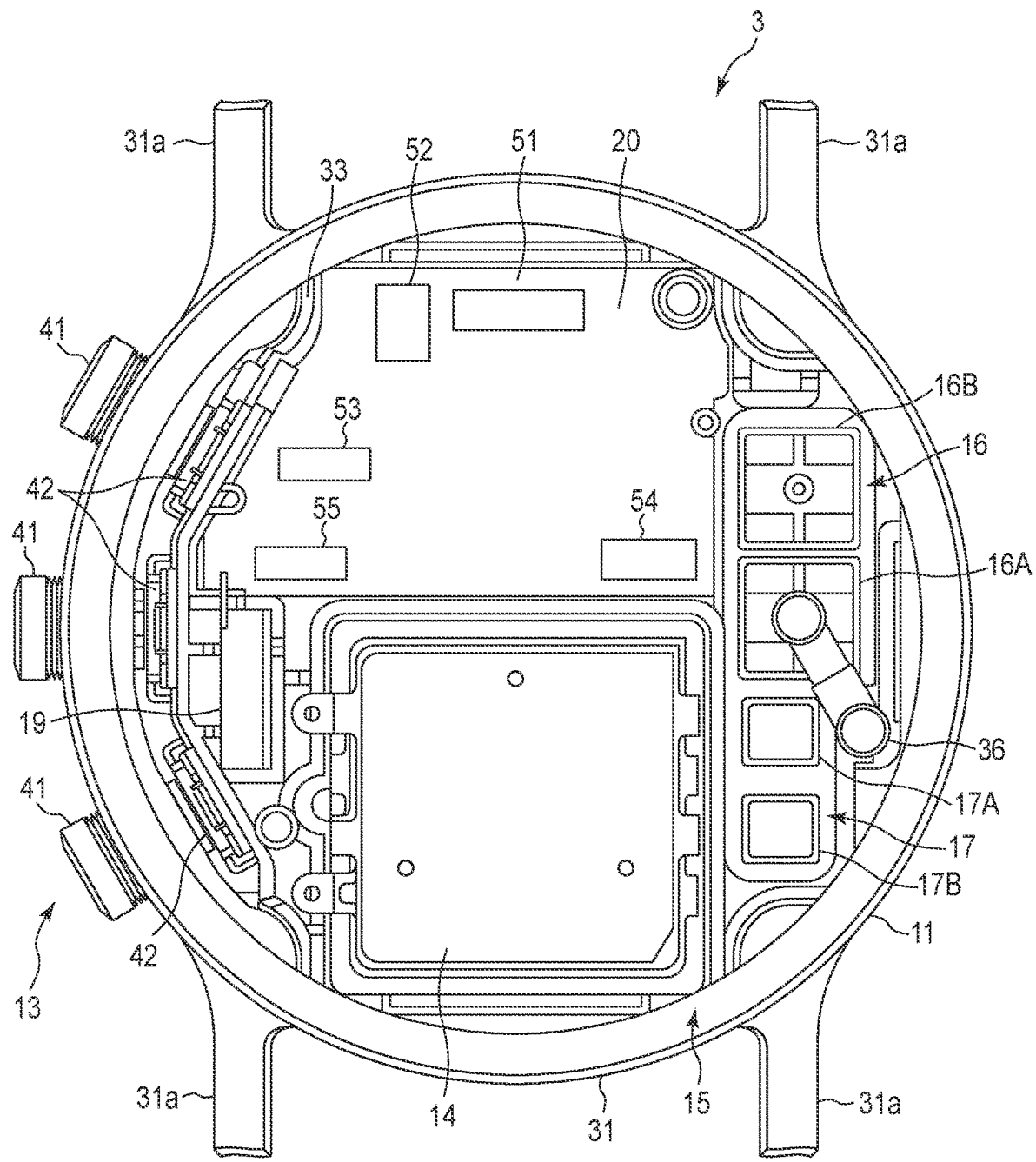
FIG. 6 is a plan view showing an internal configuration of the device body.
Figure 7:
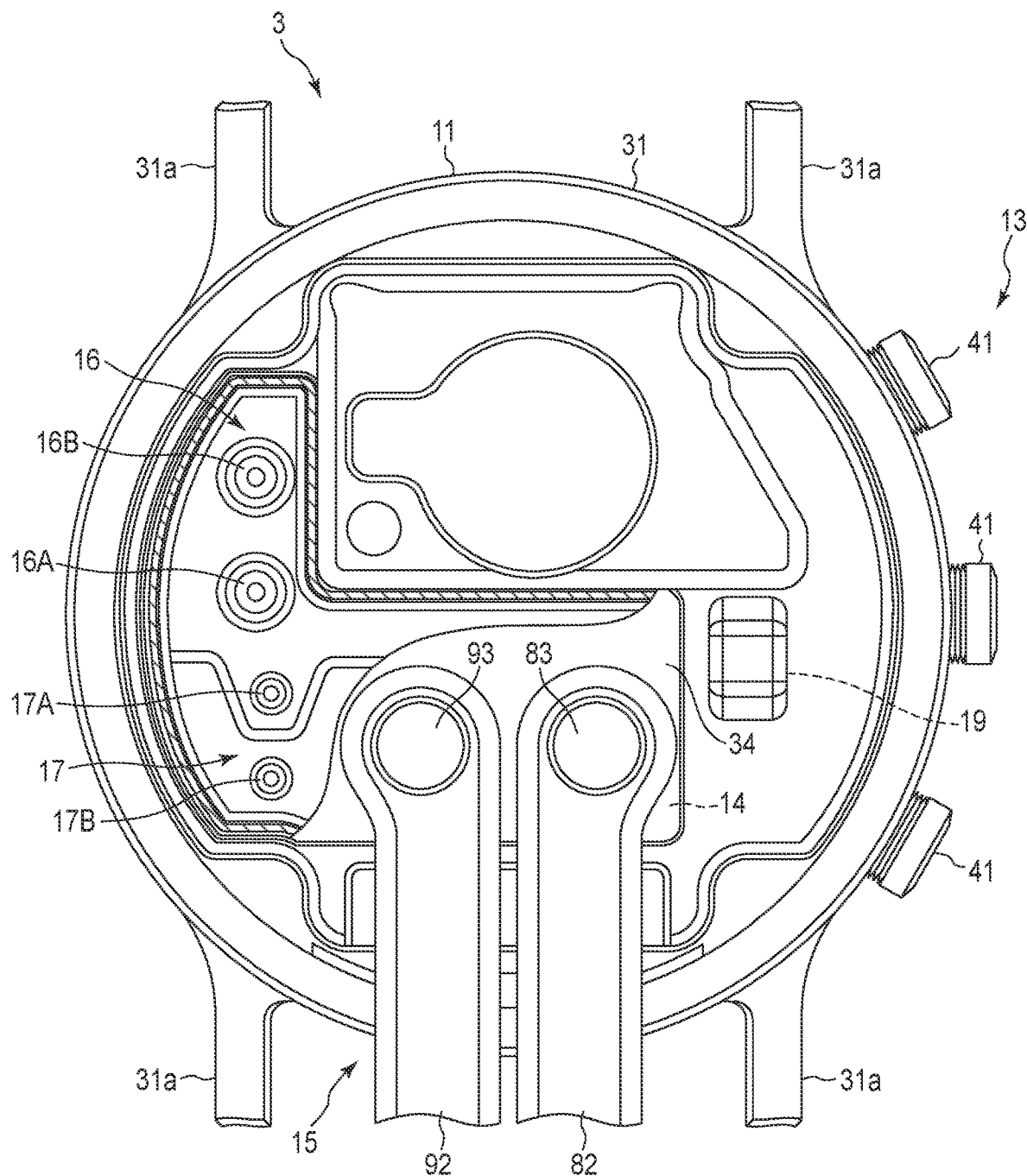
FIG. 7 is a plan view showing an internal configuration of the device body.
Figure 8:
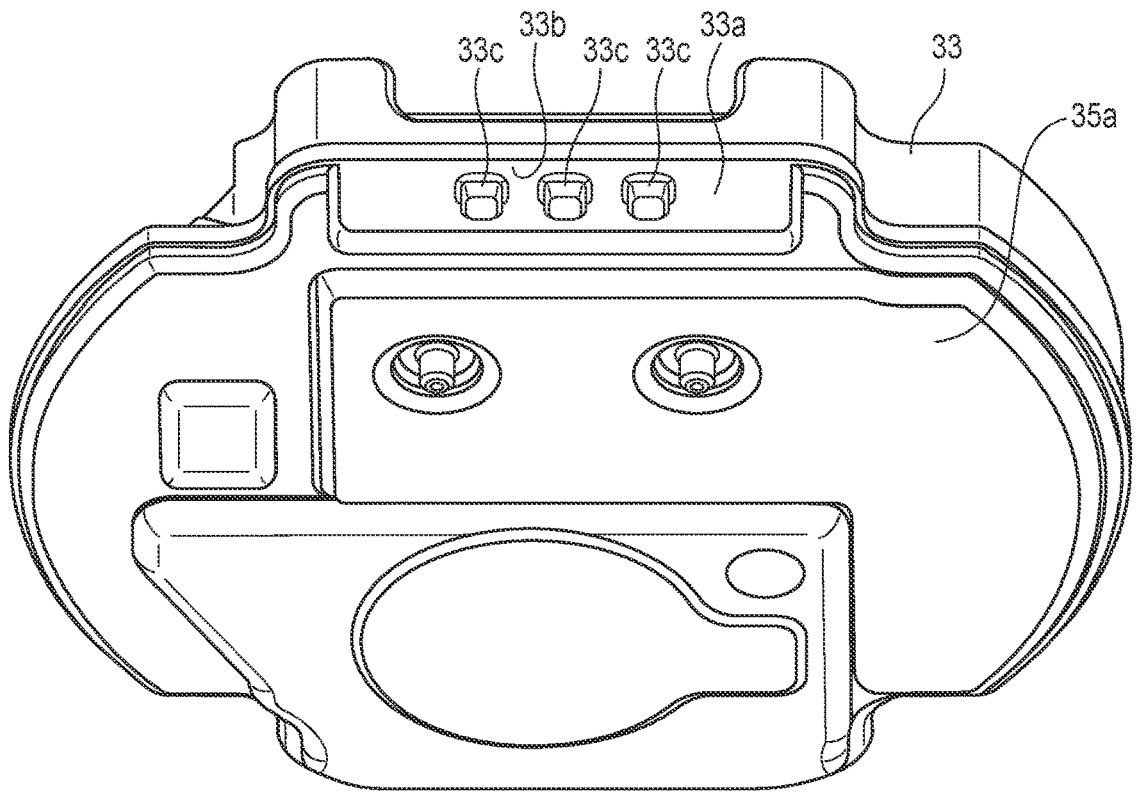
FIG. 8 is a perspective view showing a base of the blood pressure measurement device.
Figure 9:
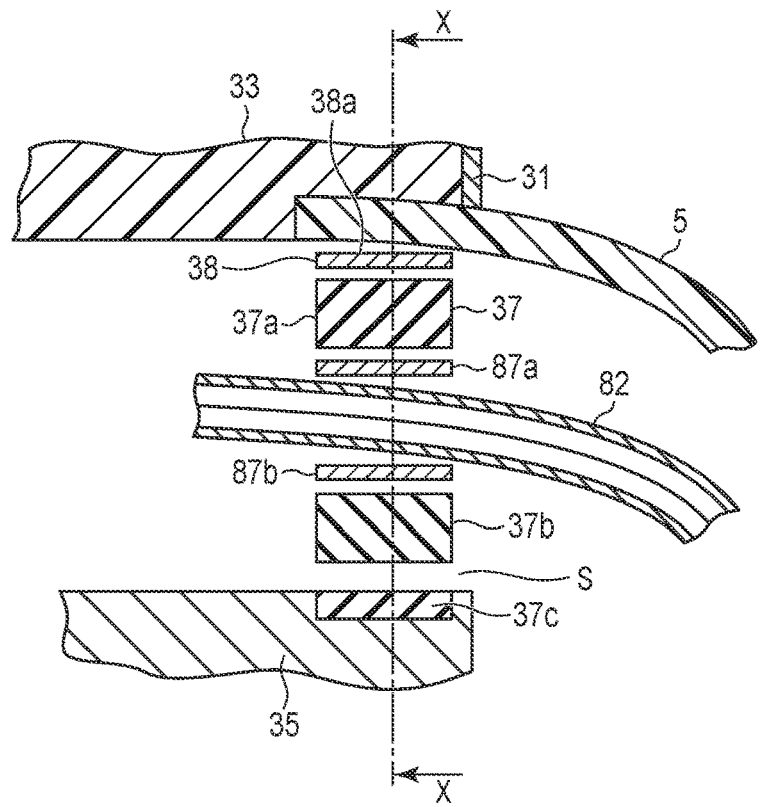
FIG. 9 is an exploded cross-sectional view showing a configuration of a major portion of a case of the blood pressure measurement device.
Figure 10:
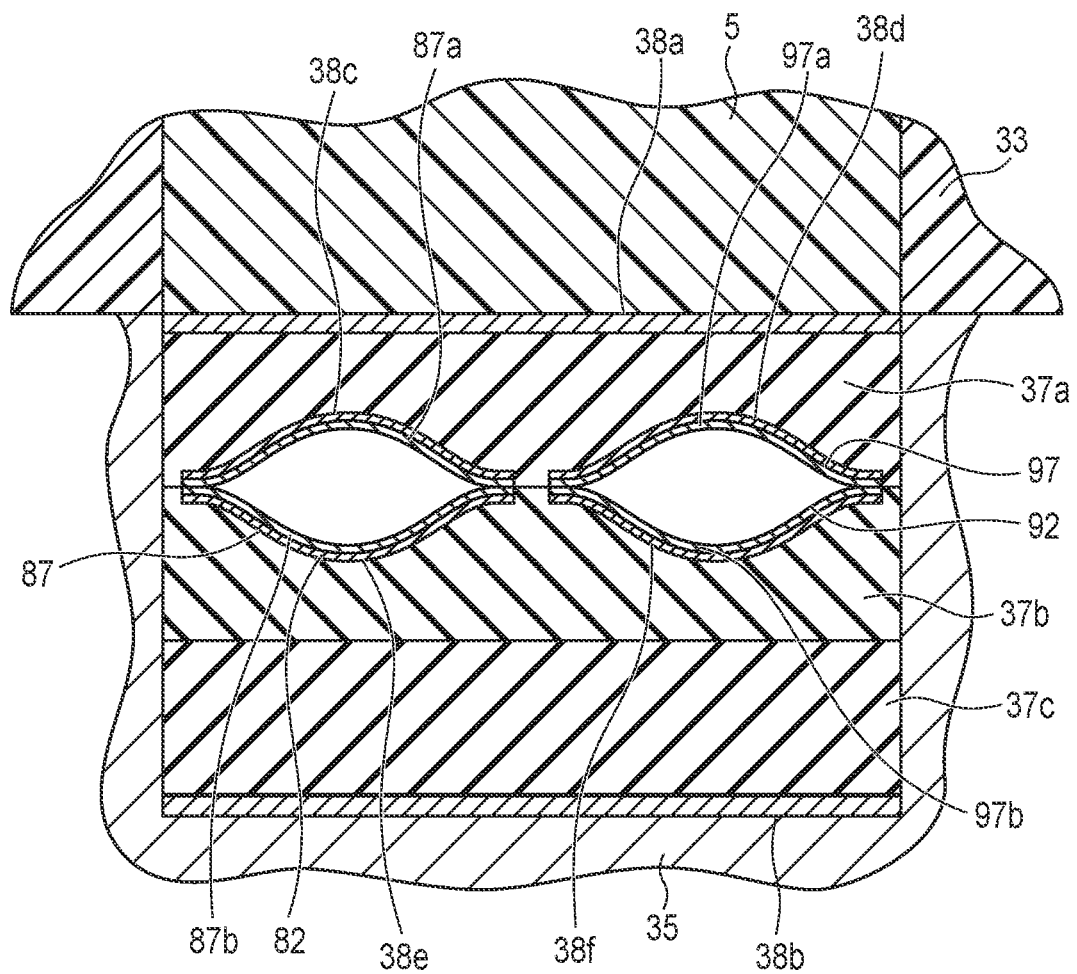
FIG. 10 is a cross-sectional view showing the major portion of the case of the blood pressure measurement device.
Figure 11:
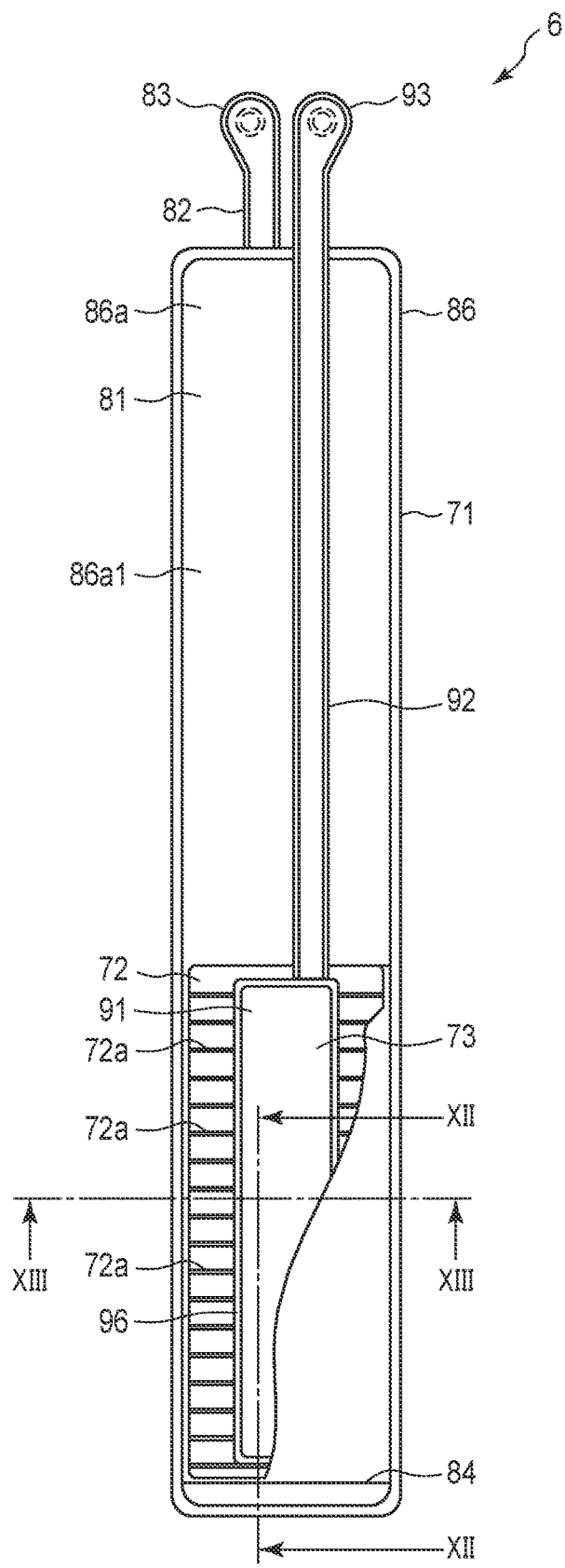
FIG. 11 is a plan view showing a configuration of a cuff structure of the blood pressure measurement device.

FIGS. 6 and 7 are plan views respectively showing how the internal structure of the device body 3 looks like when viewed from the windshield 32 side and the back cover 35 side. FIG. 8 is a perspective view showing a base 33 of the blood pressure measurement device 1. FIG. 9 is an exploded cross-sectional view schematically showing a recess 33a of the base 33 of the blood pressure measurement device 1 and the vicinity thereof. FIG. 10 is a sectional view schematically showing a section taken along line X-X in FIG. 9. FIG. 11 is a plan view showing how the configuration of the cuff structure 6 of the blood pressure measurement device 1 is when viewed from the sensing cuff 73 side.

Figure 14:
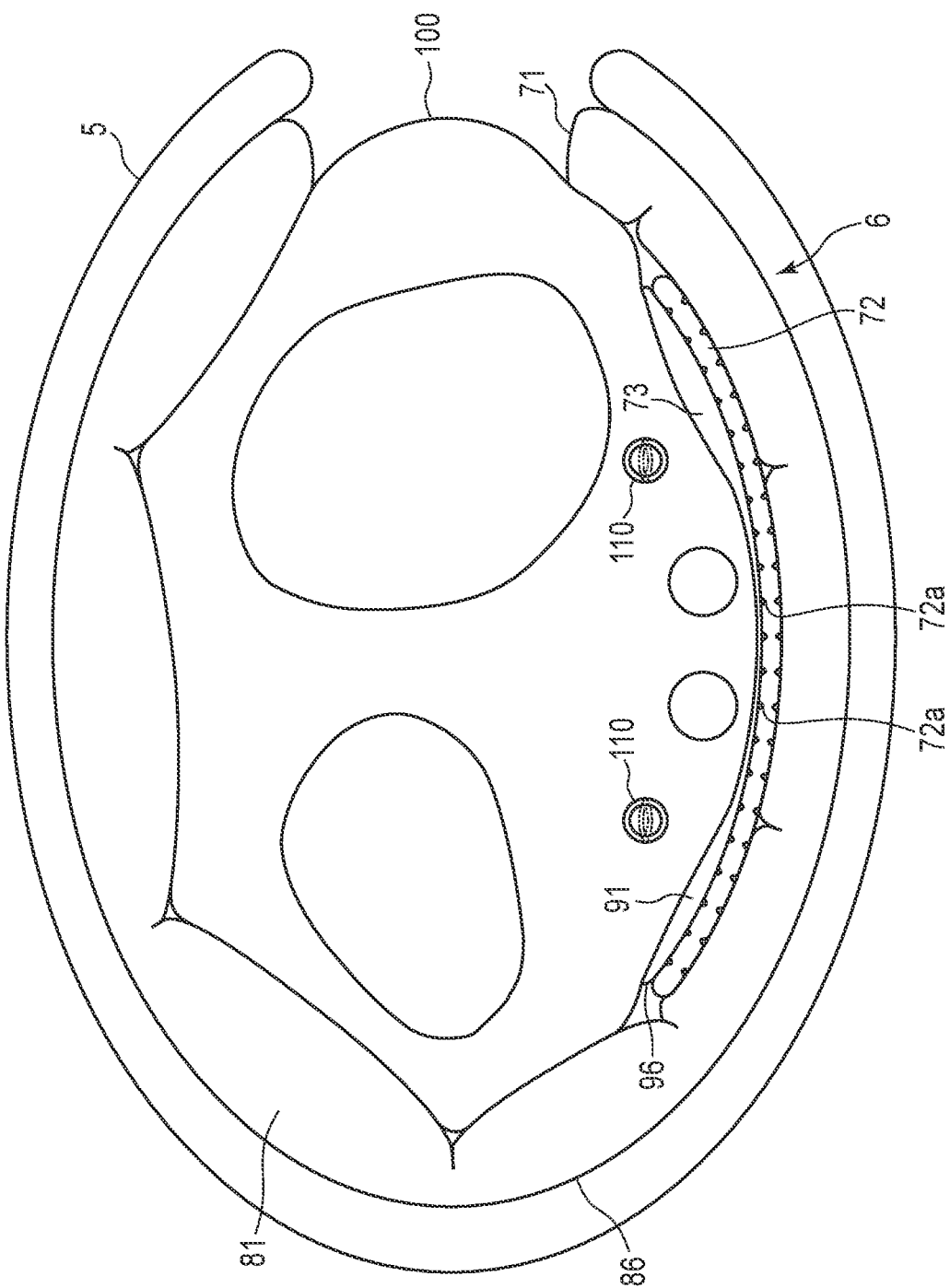
FIG. 14 is a side view schematically showing how a pressing cuff of the cuff structure is when it is inflated.

FIG. 12 is a cross-sectional view schematically showing the configuration of the curler 5 and cuff structure 6 of the blood pressure measurement device 1 in a section taken along line XII-XII in FIG. 11. FIG. 13 is a cross-sectional view showing the configuration of the curler 5 and cuff structure 6 in a section taken along line XIII-XIII in FIG. 11. FIGS. 14 and 15 are respectively a side view and a cross-sectional view schematically showing an example in which the pressing cuff 71 and sensing cuff 73 of the cuff structure 6 are inflated. In FIG. 12, the curler 5 and the cuff structure 6 are schematically shown as being linear for convenience of illustration, but actually they are curved in the configuration of the blood pressure measurement device 1.

The blood pressure measurement device 1 is an electronic blood pressure measurement device worn on a living body. The present embodiment will be described, referring to an electronic blood pressure measurement device embodied as a wearable device worn on the wrist 100 of the living body. As shown in FIGS. 1 to 15, the blood pressure measurement device 1 comprises a device body 3, a strap 4, a curler 5, a cuff structure 6 including both a pressing cuff 71 and a sensing cuff 73, and a fluid circuit 7. The pressing cuff 71 mentioned here is an example of the "cuff" of the present invention.

As shown in FIGS. 1 to 10, the device body 3 comprises a case 11, a display unit 12, an operation unit 13, a pump 14, a flow path portion 15, an on-off valve 16, a pressure sensor 17, a power supply unit 18, a vibration motor 19, and a control board 20. The device body 3 is a supply device that supplies a fluid to the pressing cuff 71 by means of the pump 14, the on-off valve 16, the pressure sensor 17, the control board 20, etc.

The case 11 comprises an outer case 31, a windshield 32 that covers an upper opening of the outer case 31, a base 33 that is provided in the lower region of the inside of the outer case 31, a flow path cover 34 that covers part of the back surface of the base 33, and a back cover 35 that covers the lower portion of the outer case 31. Also, the case 11 comprises a flow path tube 36 that constitutes part of the fluid circuit 7.

In addition, the case 11 comprises a seal member 37 that seals a gap S in which part of the curler 5 and part of the cuff structure 6 can be arranged, and a fixing member 38 that prevents the seal member 37 from coming off the outer case 31. The gap S is defined by, for example, the outer case 31, the back cover 35 and the curler 5.

The outer case 31 is formed to have a cylindrical shape. The outer case 31 includes two pairs of lugs 31a provided at the positions symmetrical in the circumferential direction of the outer peripheral surface, and spring rods 31b respectively provided between the two pairs of lugs 31a. The windshield 32 is a circular glass plate.

The base 33 holds the display unit 12, the operation unit 13, the pump 14, the on-off valve 16, the pressure sensor 17, the power supply unit 18, the vibration motor 19, and the control board 20. In addition, the base 33 constitutes part of the flow path portion 15.

As shown in FIG. 8, a recess 33a in which one end portion 5a of the curler 5 can be arranged is formed in a peripheral portion of the back surface 35a, which is the outer surface of the base 33 on the side of the back cover 35, such that the recess 33a is at a position corresponding to one pair of lugs 31a.

On the bottom surface 33b of the recess 33a, for example, a plurality of protrusions 33c that can be arranged in the hole 5b formed in the end portion 5a of the curler 5 are formed. In a specific example, three protrusions 33c are formed.

The flow path cover 34 is fixed to the back surface 35a of the base 33. The base 33 and the flow path cover 34 form part of the flow path portion 15 by providing a groove in one or both of them.

The back cover 35 covers the living body side end of the outer case 31. The back cover 35 is fixed to the outer case 31 or to the living body side end of the base 33 portion by means of, for example, four screws 35b. As shown in FIG. 5, a recess 35c that forms part of the gap S is formed in a portion of the back cover 35 that faces one pair of lugs 31a.

The flow path tube 36 constitutes part of the flow path portion 15. The flow path tube 36 connects, for example, the on-off valve 16 and part of the flow path portion 15 of the base 33.

As shown in FIGS. 9 and 10, the seal member 37 is formed of a material that has an elastic modulus lower than those of the tube 82 of the pressing cuff 71 and the tube 92 of the sensing cuff 73 arranged in the gap S and that is a gel body capable of maintaining the shape.

The seal member 37 is a member formed of a gel body. In a specific example, the seal member 37 is constituted by a first seal sheet member 37a, a second seal sheet member 37b and a third seal sheet member 37c, which are formed of a silicone gel and are elongated in one direction.

The first seal sheet member 37a is arranged between the curler 5 and part of the tube 82 of the pressing cuff 71 and part of the tube 92 of the sensing cuff 73. The second seal sheet member 37b is laid on the third seal sheet member 37c. The integrated body of the second seal sheet member 37b and the third seal sheet member 37c is arranged between the back cover 35 and part of the tube 82 of the pressing cuff 71 and part of the tube 92 of the sensing cuff 73.

The first seal sheet member 37a, the second seal sheet member 37b and the third seal sheet member 37c seal the gap S by deforming in conformity with a section defined by the recess 33a of the base 33, part of the tube 82 of the pressing cuff 71, and part of the tube 92 of the sensing cuff 73 and the back cover 35.

The elastic moduli of the first seal sheet member 37a and the second seal sheet member 37b are lower than those of part of the tube 82 of the pressing cuff 71 and part of the tube 92 of the sensing cuff 73.

The fixing member 38 is made of, for example, a plurality of double-sided adhesive tapes, and a specific example of the fixing member 38 is made of a first double-sided adhesive tape 38a, a second double-sided adhesive tape 38b, a third double-sided adhesive tape 38c, a fourth double-sided adhesive tape 38d, a fifth double-sided adhesive tape 38e, and a sixth double-sided adhesive tape 38f.

The first double-sided adhesive tape 38a is arranged between the first seal sheet member 37a and the curler 5. The first double-sided adhesive tape 38a fixes the first seal sheet member 37a to the curler 5. The first double-sided adhesive tape 38a extends, for example, from one widthwise end of the curler 5 to the other widthwise end. The first double-sided adhesive tape 38a extends from one widthwise end of the first seal sheet member 37a to the other widthwise end.

The second double-sided adhesive tape 38b is arranged between the third seal sheet member 37c and the back cover 35. The second double-sided adhesive tape 38b fixes the third seal sheet member 37c to the back cover 35. The second double-sided adhesive tape 38b extends, for example, from one widthwise end of the third seal sheet member 37c to the other widthwise end.

The third double-sided adhesive tape 38c is arranged between part of the tube 82 of the pressing cuff 71 and the first seal sheet member 37a. The third double-sided adhesive tape 38c fixes the first seal sheet member 37a to part of the tube 82 of the pressing cuff 71. The third double-sided adhesive tape 38c extends, for example, from one widthwise end of the first tube sheet member 87a, which forms part of the tube 82, to the other widthwise end.

The fourth double-sided adhesive tape 38d is arranged between the first seal sheet member 37a and part of the tube 92 of the sensing cuff 73. The fourth double-sided adhesive tape 38d fixes the first seal sheet member 37a to part of the tube 92 of the sensing cuff 73. The fourth double-sided adhesive tape 38d extends, for example, from one widthwise end of the third tube sheet member 97a, which forms part of the tube 92, to the other widthwise end.

The fifth double-sided adhesive tape 38e is arranged between the second seal sheet member 37b and part of the tube 82 of the pressing cuff 71. The fifth double-sided adhesive tape 38e fixes the second seal sheet member 37b to part of the tube 82. The fifth double-sided adhesive tape 38e extends from one widthwise end of the second tube sheet member 87b, which forms part of the tube 82, to the other widthwise end.

The sixth double-sided adhesive tape 38f is arranged between the second seal sheet member 37b and part of the tube 92. The sixth double-sided adhesive tape 38f fixes the second seal sheet member 37b to part of the tube 92. The sixth double-sided adhesive tape 38f extends from one widthwise end of the fourth tube sheet member 97b, which forms part of the tube 92, to the other widthwise end.

The display unit 12 is arranged on the base 33 of the outer case 31 and directly below the windshield 32. The display unit 12 is electrically connected to the control board 20. The display unit 12 is, for example, a liquid crystal display or an organic electroluminescence display. The display unit 12 displays various information, including a date and time, blood pressure values such as systolic blood pressure and diastolic blood pressure, and measurement results such as a heart rate.

The operation unit 13 is configured to enable commands to be entered from a user. For example, the operation unit 13 includes a plurality of buttons 41 provided on the case 11, a sensor 42 that detects an operation of the buttons 41, and a touch panel 43 provided on either the display unit 12 or the windshield 32. The operation unit 13 is operated by a user and converts a command into an electric signal. The sensor 42 and the touch panel 43 are electrically connected to the control board 20 and output an electric signal to the control board 20.

For example, three buttons 41 are provided. The buttons 41 are supported on the base 33 and protrude from the outer peripheral surface of the outer case 31. The plurality of buttons 41 and the plurality of sensors 42 are supported on the base 33. The touch panel 43 is provided, for example, integrally with the windshield 32.

The pump 14 is, for example, a piezoelectric pump. The pump 14 compresses air and supplies the compressed air to the cuff structure 6 via the flow path portion 15. The pump 14 is electrically connected to the control unit 55.

The flow path portion 15 is an air flow path configured by a groove or the like provided in a flow path cover 34 that covers the major surface on the back cover 35 side of the base 33 and on the back cover 35 side of the base 33. The flow path portion 15 constitutes a flow path that connects the pump 14 to the pressing cuff 71 and a flow path that connects the pump 14 to the sensing cuff 73. In addition, the flow path portion 15 constitutes a flow path that connects the pressing cuff 71 to the atmosphere and a flow path that connects the sensing cuff 73 to the atmosphere. The flow path cover 34 has a connected portion 34a to which the pressing cuff 71 and the sensing cuff 73 are connected. The connected portion 34a is, for example, a cylindrical nozzle provided in the flow path cover 34.

The on-off valve 16 opens or closes part of the flow path portion 15. For example, a plurality of on-off valves 16 are provided, and a combination of the open/closed states of the on-off valves 16 selectively opens or closes a flow path connecting the pump 14 to the pressing cuff 71, a flow path connecting the pump 14 to the sensing cuff 73, a flow path connecting the pressing cuff 71 to the atmosphere and a flow path connecting the sensing cuff 73 to the atmosphere. For example, two on-off valves 16 are used.

The pressure sensor 17 detects pressure of the pressing cuff 71 and the sensing cuff 73. The pressure sensor 17 is electrically connected to the control board 20. The pressure sensor 17 is electrically connected to the control board 20, converts detected pressure into an electric signal, and outputs the electric signal to the control board 20. The pressure sensor 17 is provided, for example, in a flow path connecting the pump 14 to the pressing cuff 71 and a flow path connecting the pump 14 to the sensing cuff 73. Since these flow paths are continuous with the pressing cuff 71 and the sensing cuff 73, the pressure in these flow paths is equal to the pressure in the internal spaces of the pressing cuff 71 and sensing cuff 73.

The power supply unit 18 is, for example, a secondary battery such as a lithium ion battery. The power supply unit 18 is electrically connected to the control board 20. The power supply unit 18 supplies power to the control board 20.

As shown in FIGS. 4 and 6, the control board 20 comprises, for example, a board 51, an acceleration sensor 52, a communication unit 53, a storage unit 54, and a control unit 55. The control board 20 is configured by mounting the acceleration sensor 52, the communication unit 53, the storage unit 54, and the control unit 55 on the board 51.

The board 51 is fixed to the base 33 of the case 11 with screws or the like.

The acceleration sensor 52 is, for example, a triaxial acceleration sensor. The acceleration sensor 52 outputs, to the control unit 55, an acceleration signal representing accelerations that are applied to the device body 3 in three directions orthogonal to each other. For example, the acceleration sensor 52 is used to measure the activity amount of the living body wearing the blood pressure measurement device 1 based on detected accelerations.

The communication unit 53 is configured to transmit/receive information to/from an external device wirelessly or by wire. The communication unit 53 transmits, for example, information controlled by the control unit 55 and information such as a measured blood pressure value and a pulse rate to an external device via a network. Also, the communication unit 53 receives a software update program or the like from the external device via the network and sends it to the control unit.

In the present embodiment, the network is, for example, the Internet, but the network is not limited to this, and may be a network such as a LAN (Local Area Network) in a hospital, or direct communications with an external device that are performed using a cable with a predetermined standard terminal such as USB. Therefore, the communication unit 53 may include a plurality of wireless antennas, micro USB connectors, etc.

The storage unit 54 stores in advance program data for controlling the entire blood pressure measurement device 1 and the fluid circuit 7, setting data for setting various functions of the blood pressure measurement device 1, calculation data for calculating a blood pressure value and a pulse based on the pressure measured by the pressure sensor 17, etc. Also, the storage unit 54 stores information such as a measured blood pressure value and a pulse.

The control unit 55 includes a single CPU or a plurality of CPUs, and controls the operation of the entire blood pressure measurement device 1 and the operation of the fluid circuit 7. The control unit 55 is electrically connected to the display unit 12, the operation unit 13, the pump 14, the on-off valves 16 and the pressure sensors 17, and supplies electric power to them. Further, the control unit 55 controls the operations of the display unit 12, the pump 14 and the on-off valves 16 based on electric signals output from the operation unit 13 and the pressure sensor 17.

For example, as shown in FIG. 4, the control unit 55 includes a main CPU 56 that controls the operation of the entire blood pressure measurement device 1, and a sub CPU 57 that controls the operation of the fluid circuit 7. For example, when a command for measuring blood pressure is input from the operation unit 13, the sub CPU 57 drives the pump 14 and the on-off valves 16 and sends compressed air to the pressing cuff 71 and the sensing cuff 73.

Also, the sub CPU 57 controls the driving and stopping of the pump 14 and the opening and closing of the on-off valves 16 based on electric signals output from the pressure sensor 17, such that compressed air is selectively supplied to the pressing cuff 71 and the sensing cuff 73 and such that the pressures of the pressing cuff 71 and the sensing cuff 73 are selectively decreased. The main CPU 56 obtains measurement results such as blood pressure values, e.g., systolic blood pressure and diastolic blood pressure, or a heart rate, based on electric signals output from the pressure sensor 17, and outputs an image signal corresponding to the measurement results to the display unit 12.

As shown in FIGS. 1 to 3, the strap 4 includes a first strap 61 provided for one pair of lugs 31a and the spring rod 31b, and a second strap 62 provided for the other pair of lugs 31a and the spring rod 31b.

The first strap 61 is referred to as a parent and is formed to have a band shape. The first strap 61 is includes a first hole portion 61a provided at one end portion and being orthogonal to the longitudinal direction of the first strap 61, a second hole portion 61b provided at the other end portion and being orthogonal to the longitudinal direction of the first strap 61, and a buckle 61c provided for the second hole portion 61b. The first hole portion 61a can receive the spring rod 31b inserted thereinto and has an inner diameter permitting the first strap 61 to rotate with respect to the spring rod 31b. That is, the first strap 61 is rotatably held by the outer case 31 between the pair of lugs 31a and with the spring rod 31b being within the first hole portion 61a.

The second hole portion 61b is provided at the tip end of the first strap 61.

The buckle 61c includes a rectangular frame-shaped body 61d and a stick 61e rotatably attached to the frame-shaped body 61d. One side of the frame-shaped body 61d, to which the stick 61e is attached, is inserted into the second hole portion 61b and is rotatably attached to the first strap 61.

The second strap 62 is referred to as a sword tip and is formed to have a strap shape with a width that enables insertion into the frame-shaped body 61d. The second strap 62 has a plurality of small holes 62a into which the stick 61e can be inserted. The second strap 62 has a third hole portion 62b provided at one end portion and being orthogonal to the longitudinal direction of the second strap 62. The third hole portion 62b can receive the spring rod 31b inserted thereinto and has an inner diameter permitting the second strap 62 to rotate with respect to the spring rod 31b. That is, the second strap 62 is rotatably held by the outer case 31 between the pair of lugs 31a and with the spring rod 31b being within the third hole portion 62b.

In the strap 4 mentioned above, the second strap 62 is inserted into the frame-shaped body 61d and the stick 61e is inserted into one small hole 62a, whereby the first strap 61 and the second strap 62 are integrally connected, and together with the outer case 31, form an annular shape conformable to the wrist 100 in the circumferential direction.

The curler 5 is formed of a resin material and has a band shape that curves along the circumferential direction of the wrist. The curler 5 has a hole 5b which is formed at one end 5a and into which a plurality of protrusions 33c formed on the bottom surface 33b of the recess 33a of the base 33 can be fitted. The end portion 5a is fixed to the base 33 when it is arranged in the recess 33a and the plurality of protrusions 33c are fitted in the hole 5b. Part of the curler 5 is arranged in the gap S of the case 11. The other end of the curler 5 is located close to the device body 3.

As shown in FIGS. 1 to 3 and FIG. 14, the curler 5 is formed of a resin material having a shape that is curved along the circumferential direction of the wrist 100 in a side view viewed in a direction orthogonal to the circumferential direction of the wrist, i.e., in the longitudinal direction of the wrist. The curler 5 extends from the device body such that it extends from the back of the wrist to the palm by way of one side and further to the central side of the other side. That is, the curler 5 is curved along the circumferential direction of the wrist so as to cover most of the circumferential direction of the wrist 100, and both ends of the curler 5 are away from each other by a predetermined distance.

The curler 5 has such hardness as provides both flexibility and shape retention. The flexibility mentioned here means that the shape of the curler 5 is deformed in the radial direction when an external force is applied thereto. For example, when the curler 5 is pressed by the strap 4, the curler 5 moves closer to the wrist, or the shape of the curler 5 becomes similar to that of the wrist or moves in conformity with the shape of the wrist in a side view. The shape retention means that the curler 5 can maintain a pre-fabricated shape when an external force is not applied, and in the present embodiment, the shape of the curler 5 can maintain a shape that curves along the circumferential direction of the wrist. The curler 5 is formed of a resin material. For example, the curler 5 is formed of polypropylene and has a thickness of approximately 1 mm. The curler 5 holds the cuff structure 6 along the inner surface shape of the curler 5.

As shown in FIGS. 1 to 5 and FIGS. 11 to 13, the cuff structure 6 comprises a pressing cuff 71, a back plate 72, and a sensing cuff 73. The cuff structure 6 is a structure formed by integrally stacking the pressing cuff 71, the back plate 72 and the sensing cuff 73. The cuff structure 6 is fixed to the inner surface of the curler 5.

The pressing cuff 71 is an example of a cuff. The pressing cuff 71 is fluidly connected to the pump 14 via the flow path portion 15. The pressing cuff 71 inflates and presses the back plate 72 and the sensing cuff 73 against the living body. The pressing cuff 71 comprises a plurality of air bags 81, a tube 82 that communicates with the air bags 81, and a connecting portion 83 provided at the tip of the tube 82.

The air bag 81 is a bag-shaped structure. Since the blood pressure measurement device 1 of the present embodiment is configured to use air supplied by the pump 14, a description will be given of the air bag. Where a fluid other than air is used, the bag-shaped structure may be a fluid bag such as a liquid bag.

The plurality of air bags 81 are stacked and fluidly communicate with each other in the stacking direction. In a specific example, the pressing cuff 71 includes two-layer air bags 81 that fluidly communicate with each other in the stacking direction, a tube 82 provided at one longitudinal end of one of the air bags 81, and a connecting portion 83 provided at the tip of the tube 82.

The major surface of one of the air bags 81 of the pressing cuff 71 is fixed to the inner surface of the curler 5. For example, the pressing cuff 71 is attached to the inner surface of the curler 5 with a double-sided adhesive tape or with an adhesive agent.

The two-layer air bags 8 have a rectangular shape elongated in one direction. For example, each air bag 81 is formed by combining two sheet members 86 that are elongated in one direction and welding the edges by heat. In a specific example, as shown in FIGS. 11 to 13, the two-layer air bags 81 includes, from the living body side, a first sheet member 86a, a second sheet member 86b forming the first layer air bag 81 together with the first sheet member 86a, a third sheet member 86c integrally adhered to the second sheet member 86b, and a fourth sheet member 86d forming the second layer air bag 81 together with the third sheet member 86c.

The first sheet member 86a and the second sheet member 86b form the air bag 81 by welding the peripheral portions of the four sides. The second sheet member 86b and the third sheet member 86c are arranged to face each other, and respectively include a plurality of openings 86b1 and 86c1 that fluidly connect the two air bags 81. An adhesive layer or a double-sided adhesive tape is provided on the curler 5 side outer surface of the fourth sheet member 86d, and the fourth sheet member 86d is adhered to the curler 5 with the adhesive layer or with the double-sided adhesive tape.

The third sheet member 86c and the fourth sheet member 86d form the air bag 81 by welding the peripheral portions of the four sides. Further, for example, a tube 82 that is fluidly continuous with the internal space of the air bag 81 is arranged on one side of the third sheet member 86c and the fourth sheet member 86d, and is fixed by welding. For example, the third sheet member 86c and the fourth sheet member 86d form the air bag 81 by welding the peripheral portions of the four sides, with the tube 82 arranged between the third sheet member 86c and the fourth sheet member 86d. By doing so, the tube 82 is integrally welded.

The tube 82 is connected to one of the two-layer air bags 81 and is provided at one longitudinal end of that air bag 81. In a specific example, the tube 82 is provided on the curler 5 side of the two-layer air bags 81 and at the end close to the device body 3.

The tube 82 is formed by combining two sheet members 87 that are elongated in one direction and welding the edges along the longitudinal direction by heat. In a specific example, the tube 82 includes, from the living body side, a first tube sheet member 87a, and a second tube sheet member 87b that forms a flow path together with the first tube sheet member 87a.

The tube 82 has a connecting portion 83 at the tip. The tube 82 constitutes a flow path between the device body 3 and the air bag 81 in the fluid circuit 7. The connecting portion 83 is connected to the connected portion 34a of the flow path cover 34. The connecting portion 83 is, for example, a nipple.

The back plate 72 is adhered to the outer surface 86a1 of the first sheet member 86a of the pressing cuff 71 with an adhesive layer, a double-sided adhesive tape, or the like. The back plate 72 is formed of a resin material and has a plate shape. For example, the back plate 72 is formed of polypropylene and is formed as a plate shape having a thickness of approximately 1 mm. The back plate 72 has a shape following property.

The shape-following property mentioned here refers to a function in which the back plate 72 can be deformed in conformity with the shape of the contacted portion of the wrist 100, and the contacted portion of the wrist 100 is a portion that is brought into contact with the back plate 72. The contact mentioned here includes both direct contact and indirect contact.

Therefore, the shape-following property means that the back plate 72 provided on the pressing cuff 71 or the back plate 72 provided between the pressing cuff 71 and the sensing cuff 73 is deformable such that the back plate 72 itself or the sensing cuff 73 provided on the back plate 72 is in conformity with the wrist 100 or comes into tight contact with the wrist 100.

For example, the back plate 72 has a plurality of grooves 72a on both major surfaces of the back plate 72 at opposing positions that are at equal intervals in the longitudinal direction of the back plate 72. Since the back plate 72 is thinner at portions where the grooves 72a are provided than at portions where no grooves are provided, the portions where the grooves 72a are provided are easily deformable. Thus, the back plate 72 has a shape-following property that deforms in accordance with the shape of the wrist 100. The back plate 72 has a length that covers the palm side of the wrist 100. The back plate 72 transmits a pressing force from the pressing cuff 71 to the back plate 72 side major surface of the sensing cuff 73 while conforming to the shape of the wrist 100.

The sensing cuff 73 is fixed to the living body side major surface of the back plate 72. As shown in FIG. 14, the sensing cuff 73 is brought into direct contact with that region of the wrist 100 where the artery exists. The sensing cuff 73 is formed to have the same shape as the back plate 72 or to have a shape smaller than the back plate 72, when it is viewed in the longitudinal direction and the width direction of the back plate 72. When the sensing cuff 73 is inflated, the sensing cuff 73 presses the region where the palm side artery 110 of the wrist 100 is present. The sensing cuff 73 is pressed against the living body by the inflated pressing cuff 71, with the back plate 72 interposed.

In a specific example, the sensing cuff 73 comprises one air bag 91, a tube 92 that communicates with the air bag 91, and a connecting portion 93 provided at the tip of the tube 92. The sensing cuff 73 has one major surface of the air bag 91 fixed to the back plate 72. For example, the sensing cuff 73 is attached to the living body side major surface of the back plate 72 with a double-sided adhesive tape, an adhesive layer, or the like.

The air bag 91 is a bag-shaped structure. Since the blood pressure measurement device 1 of the present embodiment is configured to use air supplied by the pump 14, a description will be given of the air bag. Where a fluid other than air is used, the bag-shaped structure may be a liquid bag or the like. A plurality of air bags 91 are stacked and fluidly communicate with each other in the stacking direction.

The air bag 91 has a rectangular shape elongated in one direction. For example, each air bag 91 is formed by combining two sheet members that are elongated in one direction and welding the edges by heat. In a specific example, as shown in FIGS. 12 and 13, the air bag 91 includes, from the living body side, a fifth sheet member 96a and a sixth sheet member 96b.

For example, a tube 92 that is fluidly continuous with the internal space of the air bag 91 is arranged on one side of the fifth sheet member 96a and the sixth sheet member 96b, and the fifth sheet member 96a and the sixth sheet member 96b are fixed by welding. For example, the fifth sheet member 96a and the sixth sheet member 96b form the air bag 91 by welding the peripheral portions of the four sides, with the tube 92 arranged between the fifth sheet member 96a and the sixth sheet member 96b. By doing so, the tube 92 is integrally welded.

The tube 92 is provided at one longitudinal end of the air bag 91. In a specific example, the tube 92 is provided at that end of the air bag 91 which is close to the device body 3. The tube 92 is formed by combining two sheet members 97 that are elongated in one direction and welding the edges along the longitudinal direction by heat. In a specific example, the tube 92 includes, from the living body side, a third tube sheet member 97a, and a fourth tube sheet member 97b that forms a flow path together with the third tube sheet member 97a.

The tube 92 formed in this manner is spaced from the tube 82 in a predetermined direction. The predetermined direction mentioned here is a direction orthogonal to the direction in which the second seal sheet member 37b is stacked on the first seal sheet member 37a of the seal member 37 when part of the tube 82 and part of the tube 92 are arranged in the gap S.

The tube 92 has a connecting portion 93 at the tip. The tube 92 constitutes a flow path between the device body 3 and the air bag 91 in the fluid circuit 7. The connecting portion 93 is connected to the connected portion 34a of the flow path cover 34. The connecting portion 93 is, for example, a nipple.

The sheet members 86, 87, 96 and 97 forming the pressing cuff 71, the tube 82, the sensing cuff 73 and the tube 92 are formed of a thermoplastic elastomer. Examples of the thermoplastic elastomer with which the sheet members 86 and 96 are formed include thermoplastic polyurethane resin (Thermoplastic PolyUrethane, hereinafter referred to as TPU), vinyl chloride resin (PolyVinyl Chloride), ethylene vinyl acetate resin (Ethylene-Vinyl Acetate), thermoplastic polystyrene resin (Thermoplastic PolyStyrene), thermoplastic polyolefin resin (Thermoplastic PolyOlefin), thermoplastic polyester resin (ThermoPlastic Polyester), and thermoplastic polyamide resin (Thermoplastic PolyAmide). TPU is preferably used as the thermoplastic elastomer. The sheet members may have a single-layer structure or a multi-layer structure.

The sheet members 86 and 96 are not limited to the thermoplastic elastomer, and may be a thermosetting elastomer such as silicone. Further, a combination of a thermoplastic elastomer (for example, TPU) and a thermosetting elastomer (for example, silicone) may be used.

Where the sheet members 86, 87, 96 and 97 are formed of a thermoplastic elastomer, a molding method such as T-die extrusion molding or injection molding is used. Where they are formed of a thermosetting elastomer, a molding method such as mold casting molding is used. After the sheet members are formed by the molding methods, they are sized to a predetermined shape, and the sized pieces are joined by adhesion, welding or the like, to thereby form a bag-shaped structure. Where a thermoplastic elastomer is used, a high frequency welder or laser welding is used as a joining method. Where a thermosetting elastomer is used, a molecular adhesive agent is used.

The fluid circuit 7 is constituted by the case 11, the pump 14, the flow path portion 15, the on-off valves 16, the pressure sensors 17, the pressing cuff 71, and the sensing cuff 73. A specific example of the fluid circuit 7 will be described, with the two on-off valves 16 of the fluid circuit 7 being referred to as a first on-off valve 16A and a second on-off valve 16B, and with the two pressure sensors 17 being referred to as a first pressure sensor 17A and a second pressure sensor 17B.

As shown in FIG. 4, the fluid circuit 7 includes a first flow path 7a that connects the pump 14 to the pressing cuff 71, a second flow path 7b that branches from an intermediate portion of the first flow path 7a and that connects the pump 14 to the sensing cuff 73, and a third flow path 7c that connects the first flow path 7a to the atmosphere. The first flow path 7a includes a first pressure sensor 17A. The first on-off valve 16A is provided between the first flow path 7a and the second flow path 7b. The second flow path 7b includes a second pressure sensor 17B. The second on-off valve 16B is provided between the first flow path 7a and the third flow path 7c.

In the fluid circuit 7 mentioned above, when the first on-off valve 16A and the second on-off valve 16B are closed, only the first flow path 7a is connected to the pump 14, and the pump 14 and the pressing cuff 71 are fluidly connected. In the fluid circuit 7, when the first on-off valve 16A is opened and the second on-off valve 16B is closed, the first flow path 7a and the second flow path 7b are connected, so that the pump 14 and the pressing cuff 71 are fluidly connected and the pump 14 and the sensing cuff 73 are fluidly connected. In the fluid circuit 7, when the first on-off valve 16A is closed and the second on-off valve 16B is closed, the first flow path 7a and the third flow path 7c are connected, so that the pressing cuff 71 and the atmosphere are fluidly connected. In the fluid circuit 7, when the first on-off valve 16A and the second on-off valve 16B are opened, the first flow path 7a, the second flow path 7b and the third flow path 7c are connected together, so that the pressing cuff 71, the sensing cuff 73 and the atmosphere are fluidly connected together.

In the blood pressure measurement device 1 configured in the above manner, the tube 82 of the pressing cuff 71, the tube 92 of the sensing cuff 73, and the curler 5 such as a movable portion have structures conformable to IPX5, which is a degree of protection provided by mechanical casings of electric machine devices.

Figure 17:
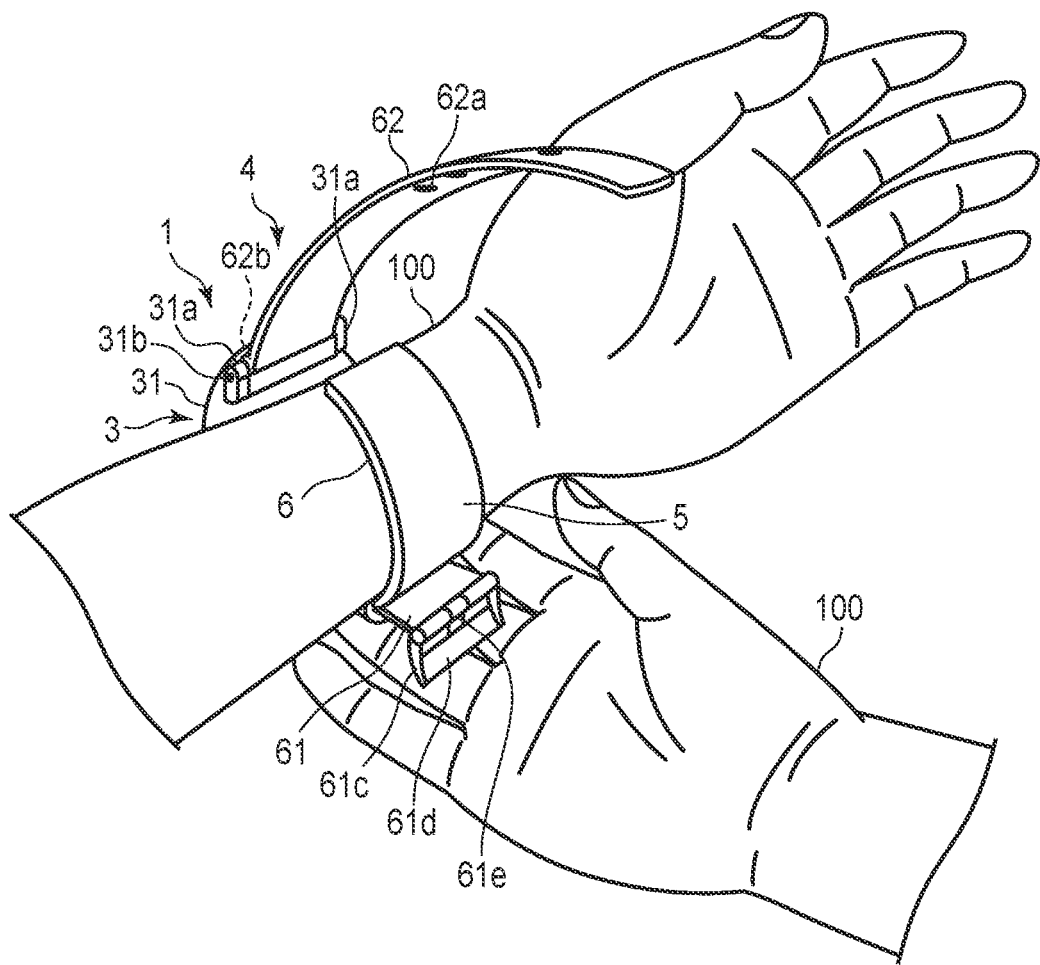
FIG. 17 is a perspective view showing an example of how the blood pressure measurement device is wrapped around the wrist.
Figure 18:
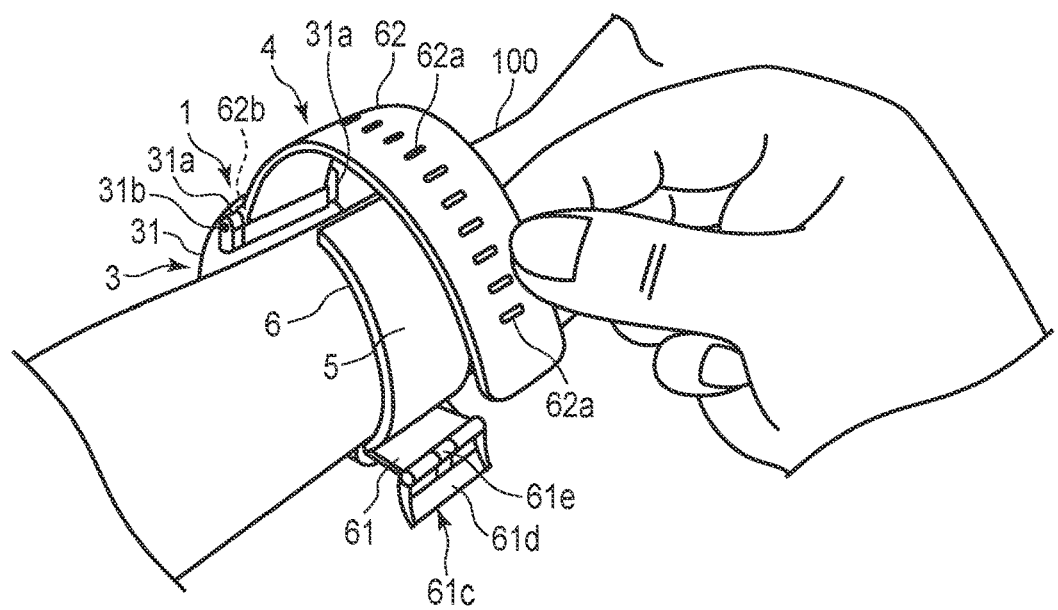
FIG. 18 is a perspective view showing an example of how the blood pressure measurement device is wrapped around the wrist.
Figure 19:
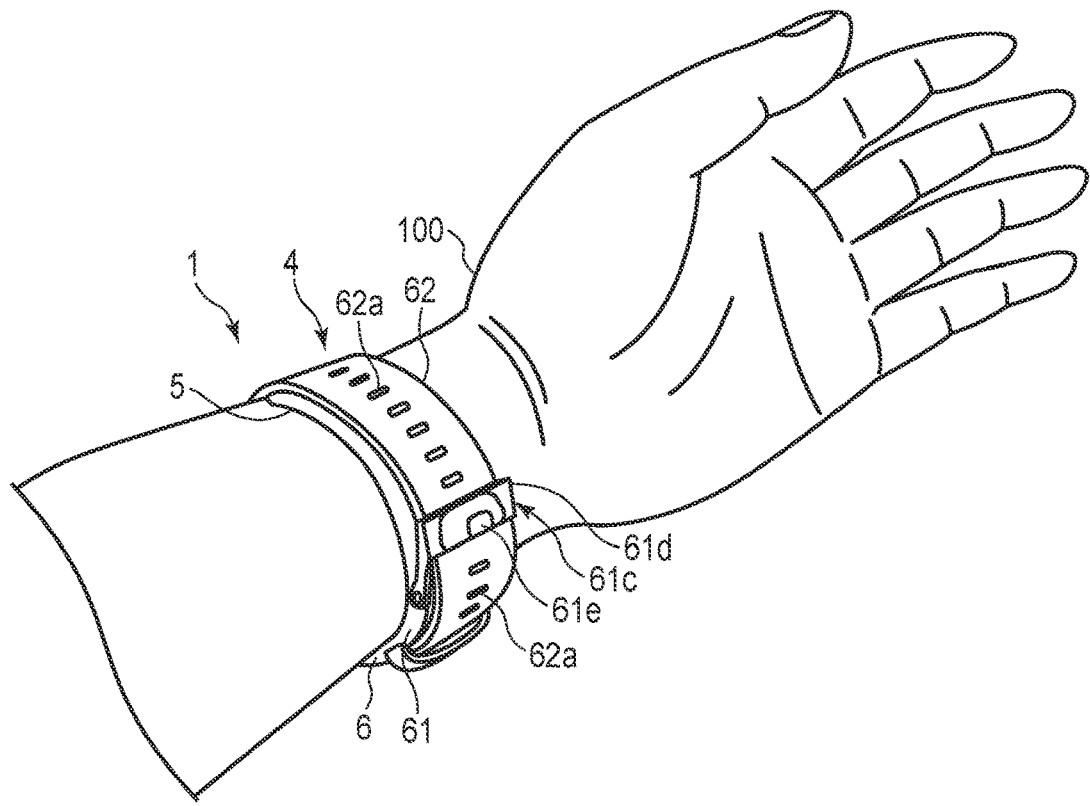
FIG. 19 is a perspective view showing an example of how the blood pressure measurement device is wrapped around the wrist.

Next, an example of how a blood pressure value is measured by the blood pressure measurement device 1 will be described with reference to FIGS. 16 to 19. FIG. 16 is a flowchart showing an example of blood pressure measurement using the blood pressure measurement device 1, and illustrates both the movement of a user and the operation of the control unit 55. FIGS. 17 to 19 show an example in which the user wears the blood pressure measurement device 1 on the wrist 100.

First, the user attaches the blood pressure measurement device 1 to the wrist 100 (step ST1). Specifically, for example, the user inserts one of the wrists 100 into the curler 5, as shown in FIG. 17.

At the time, in the blood pressure measurement device 1, the device body 3 and the sensing cuff 73 are at opposing positions of the curler 5, so that the sensing cuff 73 is arranged in the region where the palm side artery 110 of the wrist 100 exists. As a result, the device body 3 is arranged on the back side of the wrist 100. Next, as shown in FIG. 18, the user passes the second strap 62 through the frame-shaped body 61d of the buckle 61c of the first strap 61, using the hand different from the hand on which the blood pressure measurement device 1 is worn. Next, the user pulls the second strap 62 to bring the member on the inner peripheral surface side of the curler 5, that is, the cuff structure 6, into close contact with the wrist 100, and inserts the stick 61e in a small hole 62a. Thus, as shown in FIG. 19, the first strap 61 and the second strap 62 are connected, and the blood pressure measurement device 1 is attached to the wrist 100.

When the blood pressure measurement device 1 is attached to the wrist 100, the curler 5, part of the tube 82 and part of the tube 92 move within the gap S. The seal member 37 is deformed in accordance with the movement of the curler 5, part of the tube 82 and part of the tube 92. Therefore, the gap S is kept sealed even when the blood pressure measurement device 1 is worn on the wrist 100.

Next, the user operates the operation unit 13 to input a command corresponding to the start of blood pressure measurement. In response to the command input operation, the operation unit 13 outputs an electric signal corresponding to the start of measurement to the control unit 55 (step ST2). Upon receipt of the electric signal, the control unit 55 opens the first on-off valve 16A, closes the second on-off valve 16B, and drives the pump 14, so that compressed air is supplied to the pressing cuff 71 and the sensing cuff 73 via the first flow path 7a and the second flow path 7b (step ST3). As a result, the pressing cuff 71 and the sensing cuff 73 start to inflate. When the pressing cuff 71 and the sensing cuff 73 start to inflate, the tubes 82 and 92 also inflate, but the seal member 37 deforms in conformity with the inflation of the tubes 82 and 92, and the gap S is kept sealed thereby.

The first pressure sensor 17A and the second pressure sensor 17B detect the pressures of the pressing cuff 71 and the sensing cuff 73, respectively, and output electric signals corresponding to the pressures to the control unit (step ST4). Based on the received electric signals, the control unit 55 determines whether or not the pressures in the internal spaces of the pressing cuff 71 and sensing cuff 73 have reached a predetermined pressure for blood pressure measurement (step ST5). For example, if the internal pressure of the pressing cuff 71 has not reached the predetermined pressure and the internal pressure of the sensing cuff 73 has reached the predetermined pressure, then the control unit 55 closes the first on-off valve 16A and supplies compressed air through the first flow path 7a.

When both the internal pressure of the pressing cuff 71 and the internal pressure of the sensing cuff 73 have reached the predetermined pressure, the control unit 55 stops driving the pump 14 (YES in step ST5). At the time, as shown in FIG. 14, the pressing cuff 71 is sufficiently inflated, and the inflated pressing cuff 71 presses the wrist 100 and the back plate 72.

Further, the sensing cuff 73 is supplied with a predetermined amount of air so that the internal pressure becomes the pressure required for blood pressure measurement, and is thus inflated, and the back plate 72 pressed by the pressing cuff 71 presses the sensing cuff 73 against the wrist 100. Therefore, the sensing cuff 73 pushes the artery 110 in the wrist 100 and presses the artery 110 as shown in FIG. 15.

In addition, the control unit 55 controls the second on-off valve 16B to repeatedly open and close the second on-off valve 16B, or adjusts the opening of the second on-off valve 16B, such that the pressure in the internal space of the pressing cuff 71 is increased. In the process of this pressure increase, the control unit 55 obtains measurement results, such as blood pressure values, e.g., systolic blood pressure and diastolic blood pressure, a heart rate or the like, based on the electric signals output from the second pressure sensor 17B.

The timing at which the first on-off valve 16A and the second on-off valve 16B are opened and closed during blood pressure measurement can be determined as appropriate. Although a description was given referring to an example in which the control unit 55 calculates blood pressure in the pressure increasing process of the pressing cuff 71, the blood pressure may be calculated in the pressure decreasing process of the pressing cuff 71 or may be calculated in both the pressure increasing process and the pressure decreasing process of the pressing cuff 71. Next, the control unit 55 outputs image signals corresponding to the obtained measurement results to the display unit 12.

Upon receipt of the image signals, the display unit 12 displays the measurement results on the screen. The user confirms the measurement results by looking at the display unit 12. After the measurement, the user removes the stick 61*e* from the small hole 62*a*, removes the second strap 62 from the frame-shaped body 61*d*, and pulls the wrist 100 off the curler 5, thereby detaching the blood pressure measurement device 1 from the wrist 100.

In the blood pressure measurement device 1 according to the embodiment configured as described above, the gap S is sealed by the seal member 37, so that foreign matter such as water or dust is prevented from entering the case 11 through the gap S.

Furthermore, since the elastic modulus of the seal member 37 is lower than the elastic moduli of the tube 82 of the pressing cuff 71 and the tube 92 of the sensing cuff 73 arranged in the gap S, the internal space of the tube 82 and the internal space of the tube 92 are prevented from being blocked. Still further, even if the curler 5, tube 82 and tube 92 move within the gap S when the blood pressure measurement device 1 is attached to the wrist 100, the seal member 37 is deformed in accordance with the movement, so that the gap S is kept sealed.

Furthermore, even if the tubes 82 and 92 inflate when the pressing cuff 71 and the sensing cuff 73 are inflated, the seal member 37 deforms in accordance with the inflation, so that the gap S is kept sealed.

Furthermore, the fixing member 38 prevents the seal member 37 from falling out of the gap S. Still further, the fixing member 38 can be made simple by configuring the fixing member 38 with a plurality of double-sided adhesive tapes 38*a*, 38*b*, 38*c*, 38*d*, 38*e* and 38*f*.

Furthermore, by configuring the fixing member 38 with a plurality of double-sided adhesive tapes 38*a*, 38*b*, 38*c*, 38*d*, 38*e* and 38*f*, the fixing member 38 can be easily replaced at the time of the maintenance of the blood pressure measurement device 1.

Furthermore, tube 82 and tube 92 in the gap S are away from each other in the direction orthogonal to the stacking direction of the seal sheet members, so that the space between the tubes 82 and 92 can be sealed by the seal sheet members.

As described above, in the blood pressure measurement device 1 according to the embodiment, the gap S is sealed with the seal member 37, so that water or dust is prevented from entering the case 11 from the outside through the gap S.

In order to make the features of the present invention more specific, a description will be given of an example and an evaluation test. Needless to say, the scope of the present invention is not limited to the example described below.

Example 1

The base 33 of the blood pressure measurement device 1 according to the above-described embodiment was formed of polycarbonate. The curler 5 of the blood pressure measurement device 1 was formed of TPU. The double-sided adhesive tapes 38*a*, 38*b*, 38*c*, 38*d*, 38*e* and 38*f* of the blood pressure measurement device 1 are provided with a silicone adhesive agent on one major surface and an acrylic adhesive agent on the other major surface. The double-sided adhesive tapes 38*a*, 38*b*, 38*c*, 38*d*, 38*e* and 38*f* are provided such that the major surfaces provided with the silicone adhesive agent are fixed to the seal member 37, and the major surfaces provided with the acrylic adhesive agent are fixed to the curler 5, tube 82, tube 92 or the back cover 35. The first seal sheet member 37*a*, the second seal sheet member 37*b*, the third seal sheet member 37*c* and the fourth seal sheet member 37*d*, which are the seal members 37 of the blood pressure measurement device 1, were formed of a silicone gel. The back cover 35 of the blood pressure measurement device 1 was formed of SUS. Tube 82 and tube 92 of the blood pressure measurement device 1 were provided with a space maintaining tape in a portion to be arranged in the gap S. In order to make the inside of the outer case 31 visible from the windshield 32 side, the components mounted on the base 33 were removed.

[Evaluation Test]

As an evaluation test, a test was carried out for confirming that the blood pressure measurement device 1 of Example 1 had IPX5, a degree of protection provided by mechanical casings of electric machine devices. As a specific example of the evaluation test, tap water was discharged at 12.5 L/m toward the blood pressure measurement device 1 from a position three meters away from the blood pressure measurement device 1. During the water discharge, a table on which the blood pressure measurement device 1 was placed was rotated 360 degrees around a rotation axis parallel to the vertical direction.

[Results of Evaluation Test]

As a result of the evaluation test, the inside of the blood pressure measurement device 1 was observed through the windshield 32, and it was confirmed that water did not enter the blood pressure measurement device 1. Since water does not enter the case 11 from the outside through the gap S, it can be seen that the gap S is sealed by the seal member 37.

Figure 20:
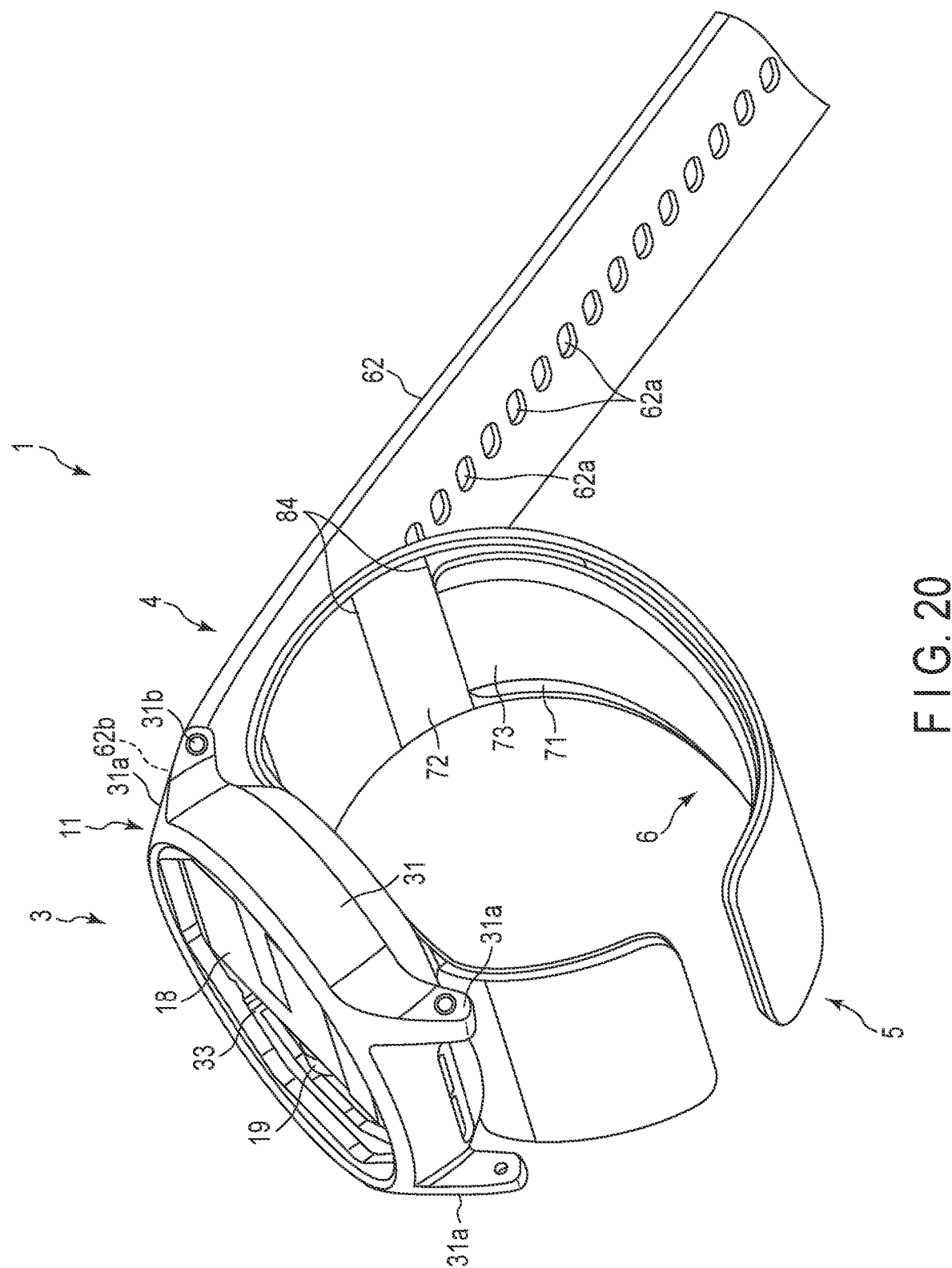
FIG. 20 is a perspective view showing another configuration of the blood pressure measurement device.

In the present embodiment, the curler 5 has its one end 5*a* housed in the case 11. As shown in FIG. 20, however, the curler 5 may be fixed to the outer surface of the back cover 35 such that its one end is projected from one pair of lugs 31*a* of the back cover 35 and the other end is projected from the other pair of lugs 31*a* and extended to a position adjacent to the one end.

In the case where the curler 5 is fixed to the outer surface of the back cover 35, the curler 5 is not arranged in the gap S, so that the gap S is defined by the base 33 and the recess 35*c* of the back cover 35. The first seal sheet member 37*a* of the seal member 37 is fixed to the base 33 by means of the double-sided adhesive tape 38*a*. Thus, the seal member 37 is provided in the gap S such that the gap S is sealed in accordance with the movable portion arranged in the gap S.

In the present embodiment, the seal member 37 includes the first seal sheet member 37*a*, the second seal sheet member 37*b* and the third seal sheet member 37*c*, but the seal member 37 may include only one seal sheet member whose thickness is equal to that of the integral combination of the second seal sheet member 37b and the third seal sheet member 37c.

Figure 21:
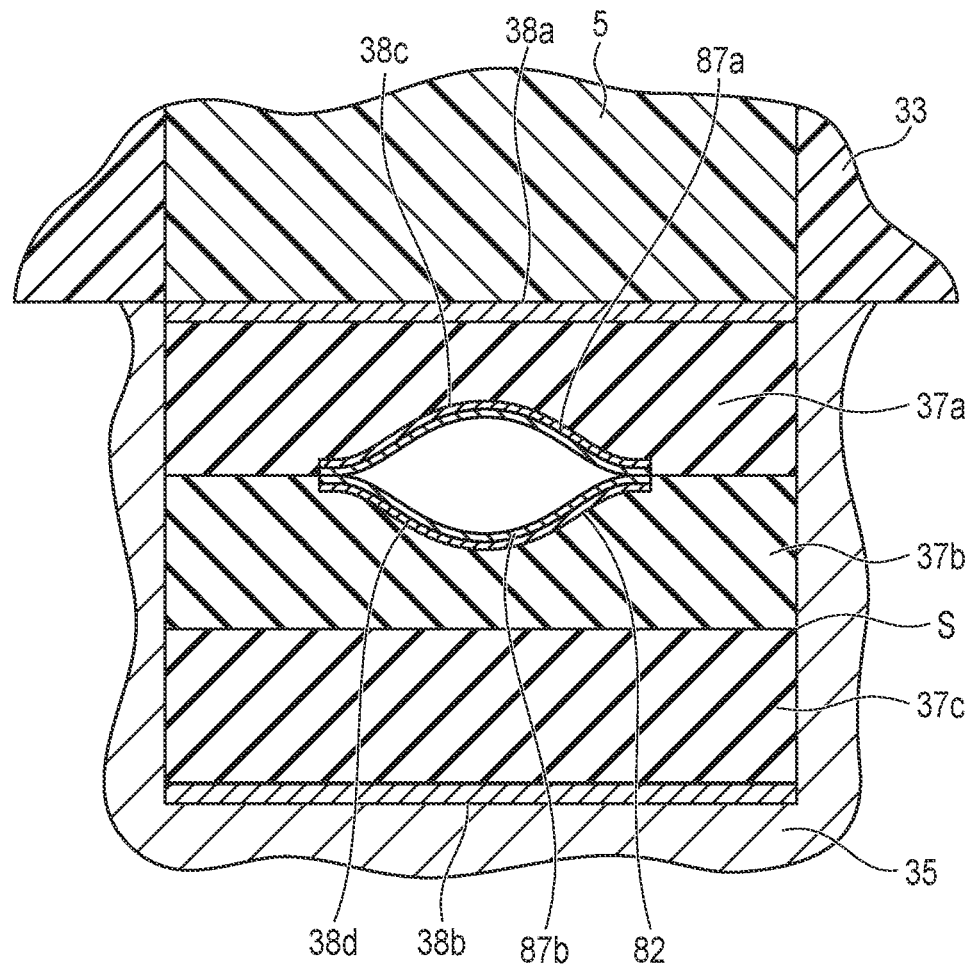
FIG. 21 is a cross-sectional view showing a major portion of a blood pressure measurement device according to a modification.
Figure 22:
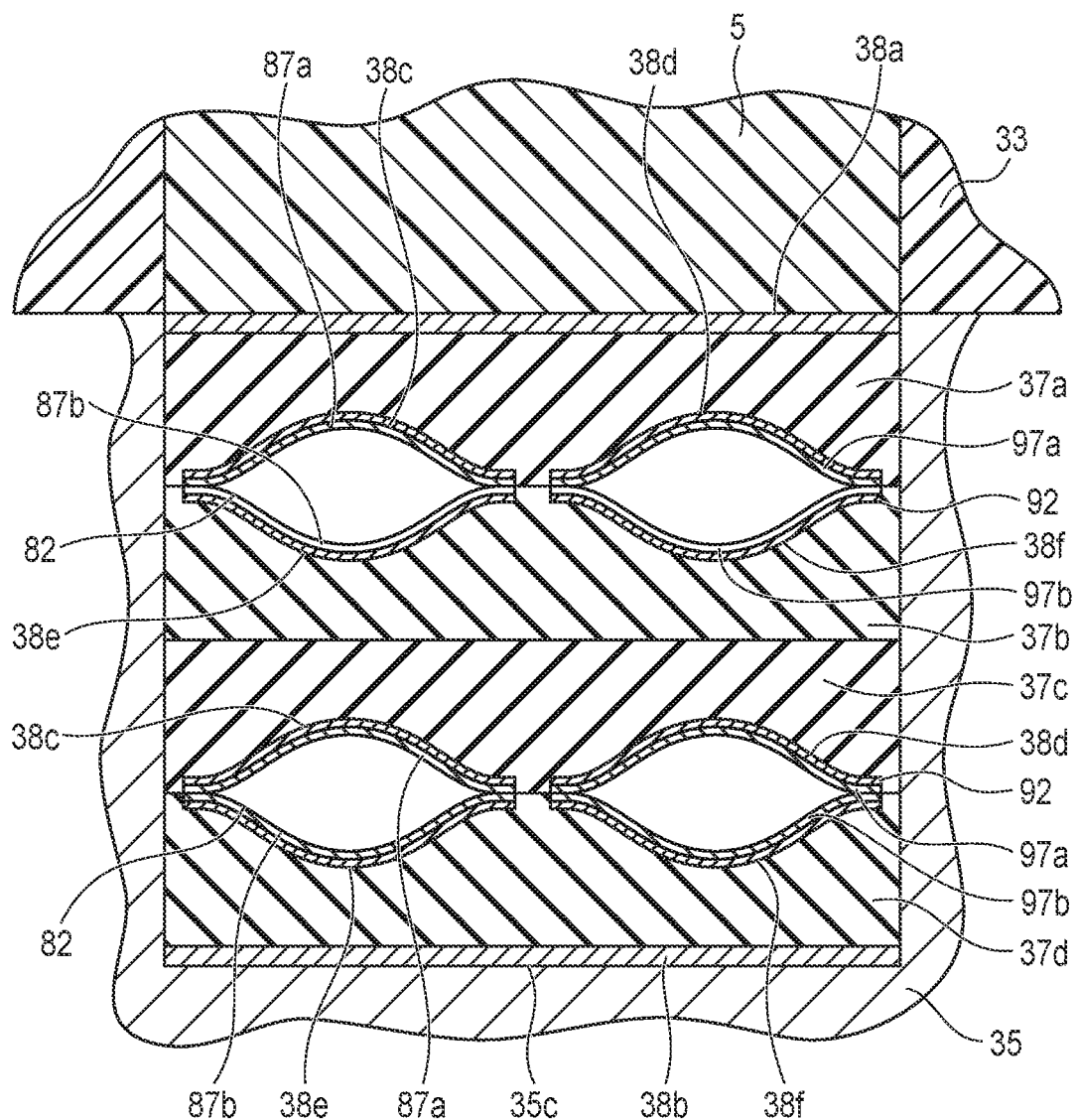
FIG. 22 is a cross-sectional view showing the major portion of the blood pressure measurement device according the modification.

In the present embodiment, the movable portion movable with respect to the case 11 and arranged in the gap S formed in the case 11 includes, for example, part of the tube 82 of the pressing cuff 71 and part of the tube 92 of the sensing cuff 73. For example, only part of one cuff may be arranged in the gap S, and as a specific example, only part of the tube 92 of the sensing cuff 73 may be arranged, as shown in FIG. 21.

Where the cuff structure 6 includes, for example, two or more cuffs, and specifically includes two pressing cuffs 71 and two sensing cuffs 73, part of the tubes 82 of the two pressing cuffs 71 and part of the tubes 92 of the two sensing cuffs 73 are arranged in the gap S, as shown in FIG. 22. These four tubes are arranged such that part of one tube 82 and part of one tube 92 are away from each other in a direction orthogonal to the stacking direction of the sheet members of the seal member 37. Part of the other tube 82 and part of the other tube 92 are arranged below the one tube 82 and the one tube 92 and are away from each other in a direction orthogonal to the stacking direction of the sheet members of the seal member 37.

In this case, the seal member 37 may include four sheet members, specifically, a first seal sheet member 37a, a second seal sheet member 37b, a third seal sheet member 37c and a fourth seal sheet member 37d. The fourth seal sheet member 37d is arranged between the third seal sheet member 37c and the recess 35c of the back cover 35.

Part of the one tube 82 and part of the one tube 92 are arranged between the first seal sheet member 37a and the second seal sheet member 37b. Part of the other tube 82 and part other tube 92 are arranged between the third seal sheet member 37c and the fourth seal sheet member 37d.

In the present embodiment, the seal member 37 includes, for example, the first seal sheet member 37a, the second seal sheet member 37b, and the third seal sheet member 37c. but the seal member 37 may be a shape-maintaining gel body that has a smaller elastic modulus than the elastic moduli of part of tube 82 and part of tube 92 arranged in the gap Sand that is integrally formed with the curler 5, the base 33 and the back cover 35.

In the present embodiment, the fixing member 38 includes the double-sided adhesive tapes 38a, 38b, 38c, 38d, 38e and 38f in one example, but in another example, an adhesive agent may be used as the fixing member 38. Alternatively, for example, a protrusion may be formed on the seal member 37, and the protrusion may be fitted into a recess formed in the curler 5 or the like to thereby form a structure for preventing the seal member 37 from coming off.

In the present embodiment, the curler 5 is fixed to the recess 33a of the base 33, and the gap S is defined by the curler 5 and the back cover 35. However, in the configuration in which the curler 5 is not fixed to the base 33, the gap S is defined, for example, by the base 33 and the back cover 35. Even in this case, the seal member 37 is only required to seal the gap S.

The above-described embodiment is merely an example of the present invention in all respects. Needless to say, various improvements and modifications can be made without departing from the scope of the present invention. That is, in implementing the present invention, a specific configuration according to the embodiment may be adopted as appropriate.

1 . . . Blood Pressure Measurement Device
3 . . . Device Body
4 . . . Strap
5 . . . Curler
5a . . . End
5b . . . Hole
6 . . . Cuff Structure
7 . . . Fluid Circuit
7a . . . First Flow Path
7b . . . Second Flow Path
7c . . . Third Flow Path
11 . . . Case
12 . . . Display Unit
13 . . . Operation Unit
14 . . . Pump
15 . . . Flow Path Portion
16 . . . On-Off Valve
16A . . . First On-Off Valve
16B . . . Second On-Off Valve
17 . . . Pressure Sensor
17A . . . First Pressure. Sensor
17B . . . Second Pressure Sensor
18 . . . Power Supply Unit
19 . . . Vibration Motor
20 . . . Control Board
31 . . . Outer Case
31a . . . Lug
31b . . . Spring Rod
32 . . . Windshield
33 . . . Base
33a . . . Recess
33b . . . Bottom Surface
33c . . . Protrusion
34 . . . Flow Path Cover
34a . . . Connected Portion
35 . . . Back Cover
35a . . . Back Surface
35b . . . Screw
35c . . . Recess
36 . . . Flow Path Tube
37 . . . Seal Member
37a . . . First Seal Sheet Member
37b . . . Second Seal Sheet Member
37c . . . Third Seal Sheet Member
37d . . . Fourth Seal Sheet Member
38 . . . Fixing Member
38a . . . First Double-Sided Adhesive Tape
38b . . . Second Double-Sided Adhesive Tape
38c . . . Third Double-Sided Adhesive Tape
38d . . . Fourth Double-Sided Adhesive Tape
38e . . . Fifth Double-Sided Adhesive Tape
38f . . . Sixth Double-Sided Adhesive Tape
41 . . . Button
42 . . . Sensor
43 . . . Touch Panel
51 . . . Board
52 . . . Acceleration Sensor
53 . . . Communication Unit
54 . . . Storage Unit
55 . . . Control Unit
61 . . . First Strap
61a . . . First Hole Portion
61b . . . Second Hole Portion
61c . . . Buckle
61d . . . Frame-Shaped Body
61e . . . Stick
62 . . . Second Strap
62a . . . Small Hole
71 . . . Pressing Cuff 72 . . . Back Plate
72a . . . Groove
73 . . . Sensing Cuff
81 . . . Air Bag
82 . . . Tube
83 . . . Connecting Portion
86 . . . Sheet Member
86a . . . First Sheet Member
86a1 . . . Outer Surface
86b . . . Second Sheet Member
86b1 . . . Opening
86c . . . Third Sheet Member
86c1 . . . Opening
86d . . . Fourth Sheet Member
87 . . . Sheet Member
87a . . . First Tube Sheet Member
87b . . . Second Tube Sheet Member
91 . . . Air Bag
92 . . . Tube
93 . . . Connecting Portion
96 . . . Sheet Member
96a . . . Fifth Sheet Member
96b . . . Sixth Sheet Member
97 . . . Sheet Member
97a . . . Third Tube Sheet Member
97b . . . Fourth Tube Sheet Member
100 . . . Wrist
110 . . . Artery
S . . . Gap

What is claimed is:

1. A blood pressure measurement device comprising:
a case including an outer case, a base housed in the outer case, and a back cover that covers an opening of the outer case;
a movable portion arranged in a gap between the outer case, the base and the back cover, and the movable portion including an inflatable cuff comprising (i) a tube, part of an inflating portion of the tube being arranged in the gap, wherein the part of the inflating portion is configured to inflate and expand in the gap, and (ii) an air bag that is in fluid communication with the tube; and
a seal member comprising at least two seal sheet members that are each formed of a gel body having a lower elastic modulus than that of the cuff, the seal member being provided in the gap to seal the gap;
wherein the part of the inflating portion of the tube is arranged in the gap between two adjacent seal sheet members among the at least two seal sheet members,
wherein the seal member is configured to deform due to inflation of the inflating portion of the tube,
wherein the inflating portion of the tube includes a plurality of tube sheet members, separate from the seal sheet members, the plurality of tube sheet members being welded to each other at edges of the tube sheet members, and
wherein the air bag includes a plurality of air bag sheet members, separate from the at least two seal sheet members, the plurality of air bag sheet members being welded to each other at edges of the plurality of air bag sheet members.

2. The blood pressure measurement device according to claim 1, wherein:
the seal member is fixed inside the gap, and the cuff is fixed to the seal member by a double-sided adhesive tape.

* * * * *